(12) United States Patent
Williams et al.

(10) Patent No.: US 8,945,091 B2
(45) Date of Patent: Feb. 3, 2015

(54) BREAKAWAY COUPLING ASSEMBLY

(75) Inventors: Randall Scott Williams, Minneapolis, MN (US); Patrick Thomas Gerst, Oakdale, MN (US)

(73) Assignee: Colder Products Company, St. Paul, MN (US)

(*) Notice: Subject to any disclaimer, the term of this patent is extended or adjusted under 35 U.S.C. 154(b) by 256 days.

(21) Appl. No.: 13/334,651

(22) Filed: Dec. 22, 2011

(65) Prior Publication Data

US 2012/0161051 A1  Jun. 28, 2012

Related U.S. Application Data

(60) Provisional application No. 61/426,187, filed on Dec. 22, 2010.

(51) Int. Cl.
*A61M 25/16* (2006.01)
*A61M 25/18* (2006.01)
*A61M 39/00* (2006.01)
*A61M 39/10* (2006.01)
(Continued)

(52) U.S. Cl.
CPC .............. *A61M 39/10* (2013.01); *F16L 37/084* (2013.01); *F16L 37/34* (2013.01);
(Continued)

(58) Field of Classification Search
CPC ..... F16L 37/32; F16L 37/252; F16L 55/1015; F16L 29/04; F16L 37/36; F16L 29/00; F16L 29/02; F16L 37/02; F16L 37/113
USPC ................ 251/149, 149.1, 149.6, 149.7, 150; 137/231, 515.5, 798, 799, 921; 141/386; 604/533–535, 537; 285/140.1, 148.5, 286.2, 331, 382.5, 285/382.7, 304, 305, 314, 239, 242
See application file for complete search history.

(56) References Cited

U.S. PATENT DOCUMENTS 3,640,552 A * 2/1972 Demler et al. ................ 285/110
5,104,157 A   4/1992 Bahner
(Continued)

FOREIGN PATENT DOCUMENTS

DE  43 05 609 A1  11/1993
WO  03-076001 A2   9/2003
(Continued)

OTHER PUBLICATIONS

International Search Report and Written Opinion issued in PCT/US2011/066951, mailed Apr. 2, 2012, 11 pages.

*Primary Examiner* — John K Fristoe, Jr.
*Assistant Examiner* — Hailey K Do
(74) *Attorney, Agent, or Firm* — Merchant & Gould P.C.

(57) ABSTRACT

A breakaway coupling assembly includes a male coupling and a female coupling. The male coupling includes ribs that flex portions of the female coupling as an insert of the male coupling is positioned within the female coupling. Once the insert of male coupling is positioned into the female coupling a predefined distance, the ribs snap into a circumferential retention groove of the female coupling to secure the male coupling to the female coupling and form a fluid seal. The male coupling is decoupled from the female coupling by pinching the female coupling to release the ribs from the retention groove.

17 Claims, 40 Drawing Sheets

(51) Int. Cl.
  *F16L 37/00* (2006.01)
  *F16L 37/28* (2006.01)
  *F16L 37/084* (2006.01)
  *F16L 37/34* (2006.01)
  *F16L 55/10* (2006.01)

(52) U.S. Cl.
  CPC .................................. *F16L 55/1015* (2013.01)
  USPC ........... 604/533; 604/534; 604/535; 285/305; 251/149; 251/149.9

(56) References Cited

U.S. PATENT DOCUMENTS 5,695,221 A * 12/1997 Sunderhaus ..................... 285/1
6,726,672 B1 4/2004 Hanly et al.
2005/0199297 A1 9/2005 Nimberger

FOREIGN PATENT DOCUMENTS

WO 2006-122406 A1 11/2006
WO 2010-034470 A1 4/2010

* cited by examiner

BREAKAWAY COUPLING ASSEMBLY

BACKGROUND

Coupling assemblies typically include female and male couplings that are connected to create a fluid flow path therebetween. Such coupling assemblies can be used in various applications, including biomedical applications, beverage dispensing, instrument connections, photochemical handling, and others.

One concern with current coupling assemblies, such as those employing Luer Lock connections, is that it is difficult to connect the female coupling and male coupling to form a seamless fluid flow channel. Further, it can be difficult to make a connection, since the female and male couplings are keyed such that the male coupling must be inserted into the female coupling at a given orientation. Finally, such connections can have the disadvantage of potential misconnection and providing little or no ability to break the connection when an intentional or otherwise inadvertent load is applied to either the coupling assembly or the fluid lines extending therefrom.

DESCRIPTION OF THE DRAWINGS

Reference is now made to the accompanying drawings, which are not necessarily drawn to scale.

DETAILED DESCRIPTION

The present disclosure relates to a breakaway coupling assembly including a male coupling and a female coupling. The male coupling includes one or more ribs that flex portions of the female coupling as the male coupling is inserted into the female coupling. Once the male coupling is positioned into the female coupling a predefined distance, the ribs snap into a circumferential retention groove of the female coupling to secure the male coupling to the female coupling and form a fluid seal. The male coupling is decoupled from the female coupling by pinching the female coupling to release the ribs from the retention groove or by pulling on ends of the respective coupling halves.

In some examples, a geometry and relationship of the ribs and retention groove can be selectively defined such that a desired amount of force is required to couple and decouple the male coupling and female coupling.

Figure 1:
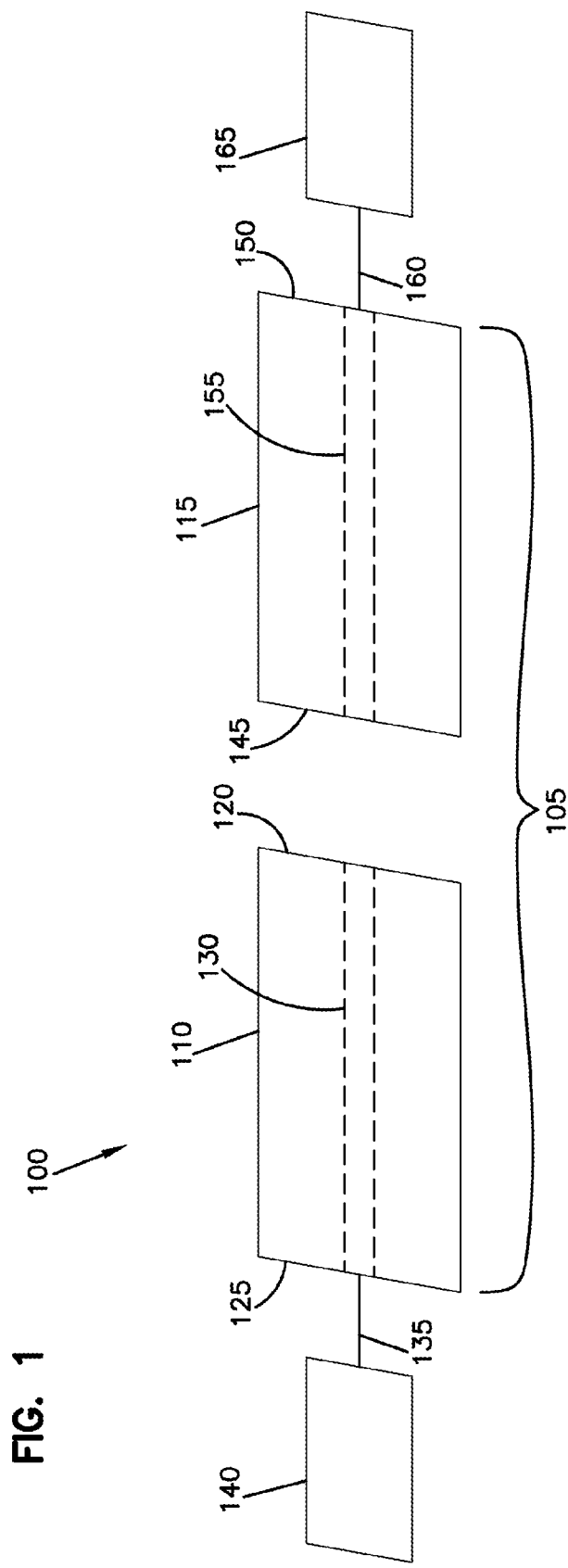
FIG. 1 is a schematic view of an example system including an example breakaway coupling assembly.
Figure 2:
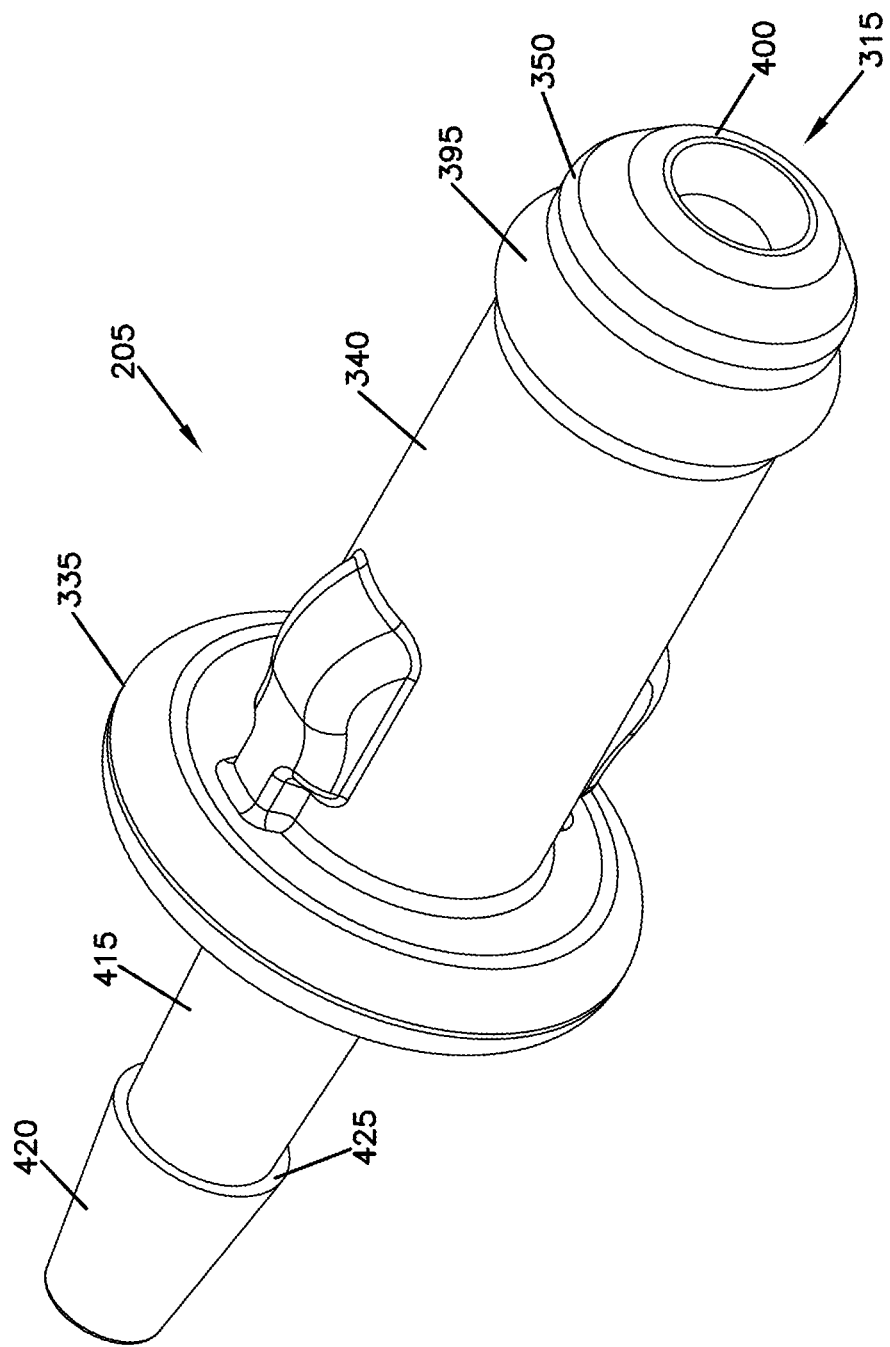
FIG. 2 is a perspective view of an example male coupling.
Figure 3:
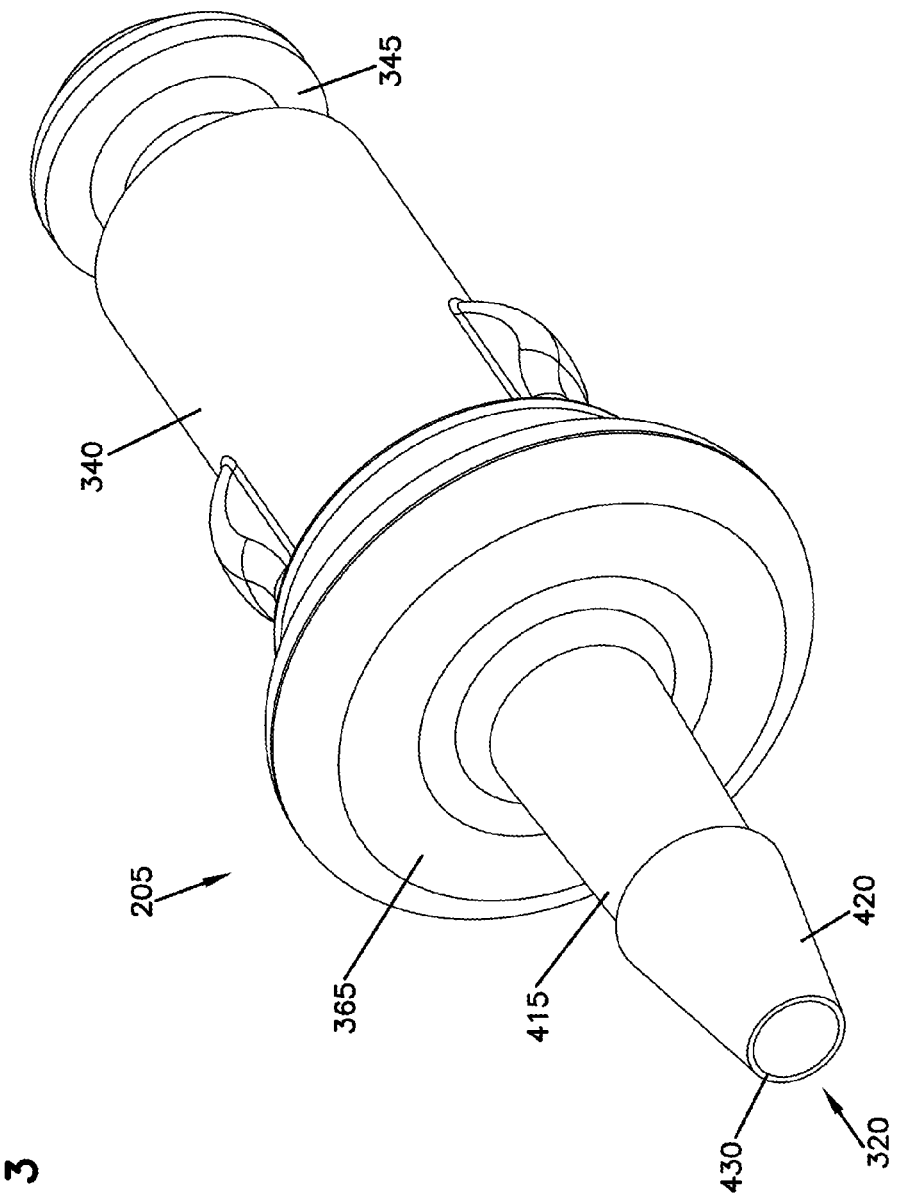
FIG. 3 is another perspective view of the male coupling of FIG. 2.

Referring now to FIG. 1, an example system 100 including a breakaway coupling assembly 105 is shown. The example assembly 105 includes a male coupling 110 and a female coupling 115.

The example male coupling 110 includes a first end 120 and an opposite second end 125 connected by an internal channel 130 formed within the male coupling 110. In the example shown, the second end 125 of the male coupling 110 is connected to a first conduit 135, which in turn is connected to a source 140.

Similarly, the example female coupling 115 includes a first end 145 and an opposite second end 150 connected by an internal channel 155 formed within the female coupling 115.

The second end 150 of the female coupling 115 is connected to a second conduit 160, which in turn is connected to a receptacle 165.

In general, the male coupling 110 and the female coupling 115 are mated by connecting the first end 120 of the male coupling 110 to the first end 145 of the female coupling 115 to form a continuous fluid flow path to allow fluid (e.g., liquids, gases) to flow from the source 140 to the receptacle 165. In some embodiments, the breakaway coupling assembly 105 is a non-valved assembly (see FIGS. 1-19). In other embodiments, the breakaway coupling assembly 105 is a valved assembly (see FIGS. 20-40). Other embodiments of the example system 100 are possible as well.

FIGS. 2-19 illustrate a first example breakaway coupling assembly 200 according to the principles of the present disclosure. The example assembly 200 is a non-valved assembly and includes a male coupling 205 and a female coupling 210.

Figure 6:
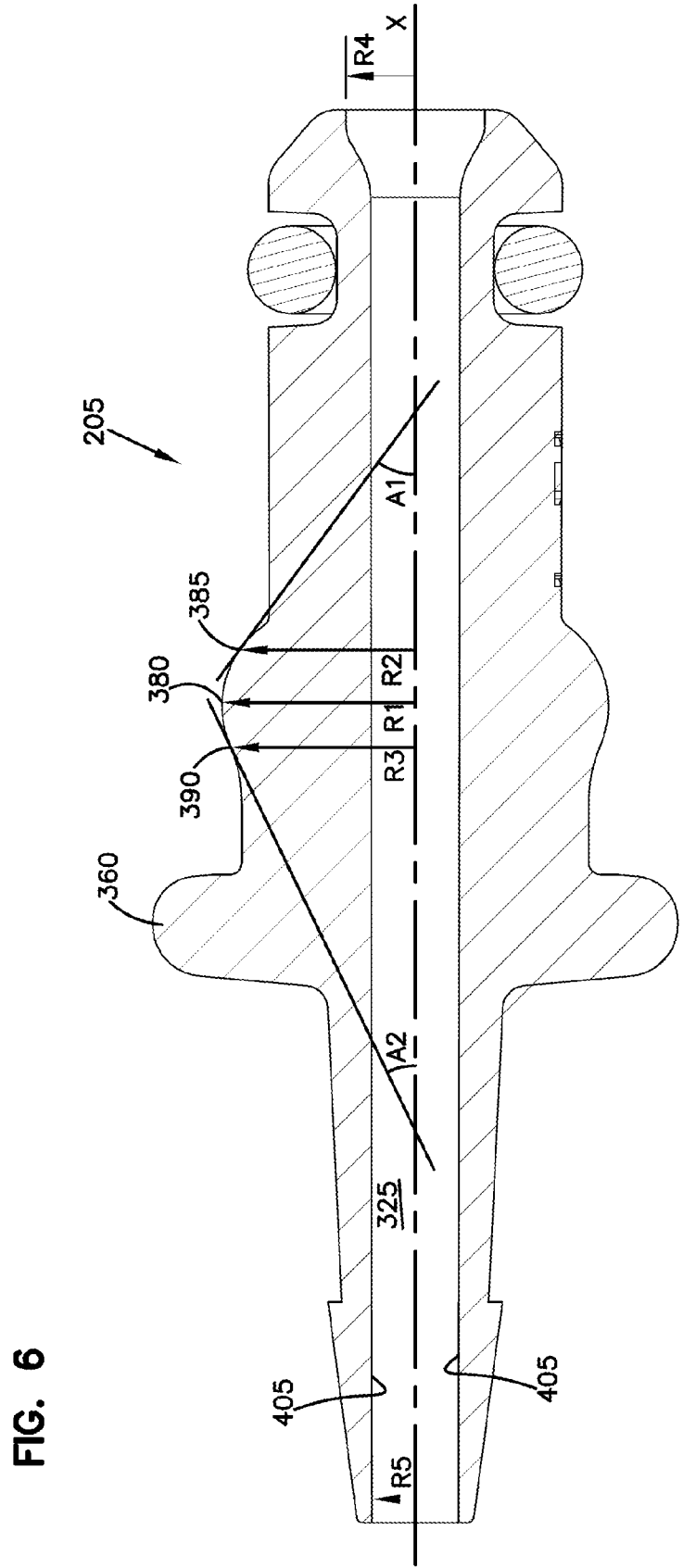
FIG. 6 is a cross-sectional view of the male coupling of FIG. 5.
Figure 7:
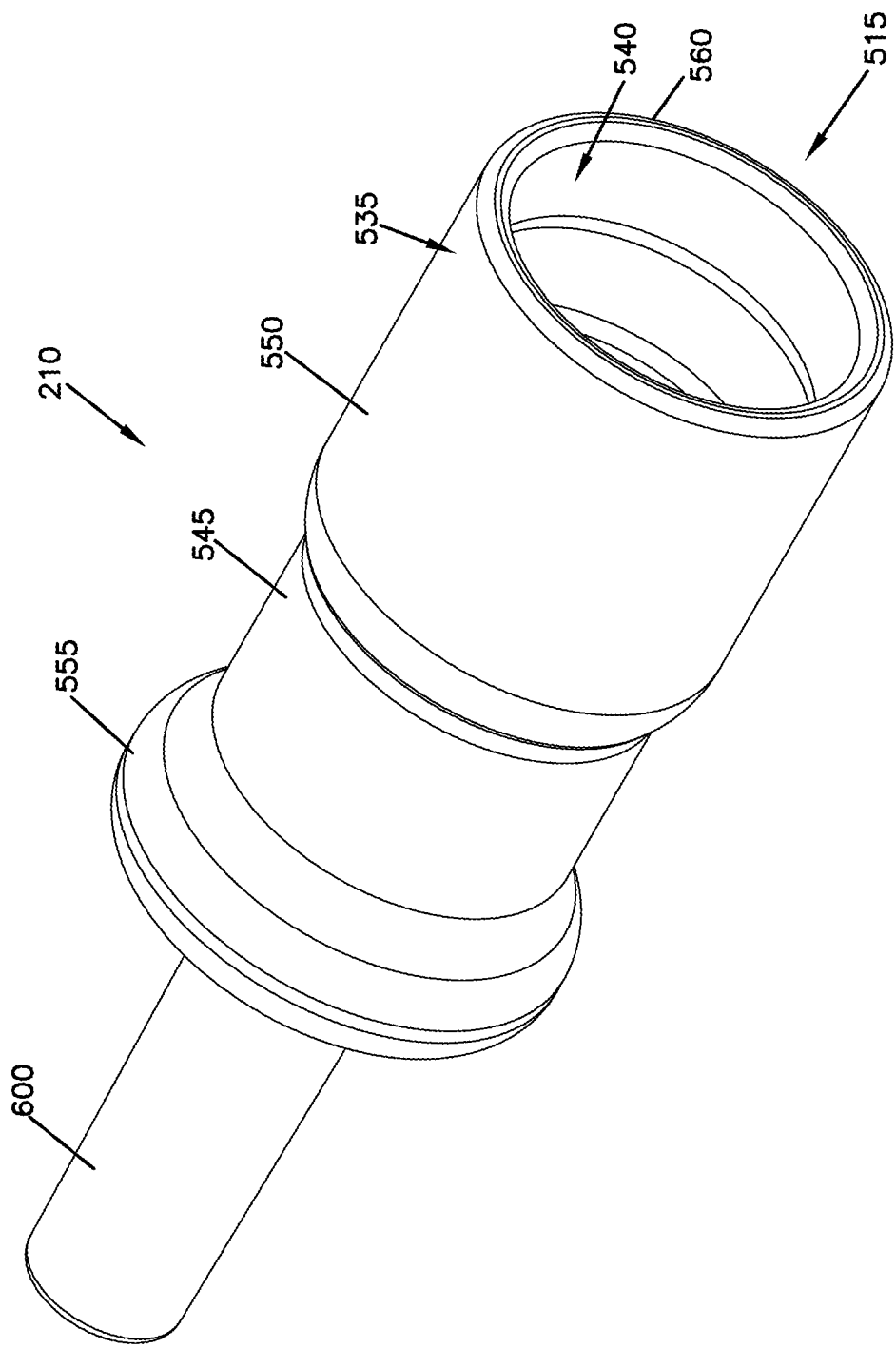
FIG. 7 is a perspective view of an example female coupling.
Figure 8:
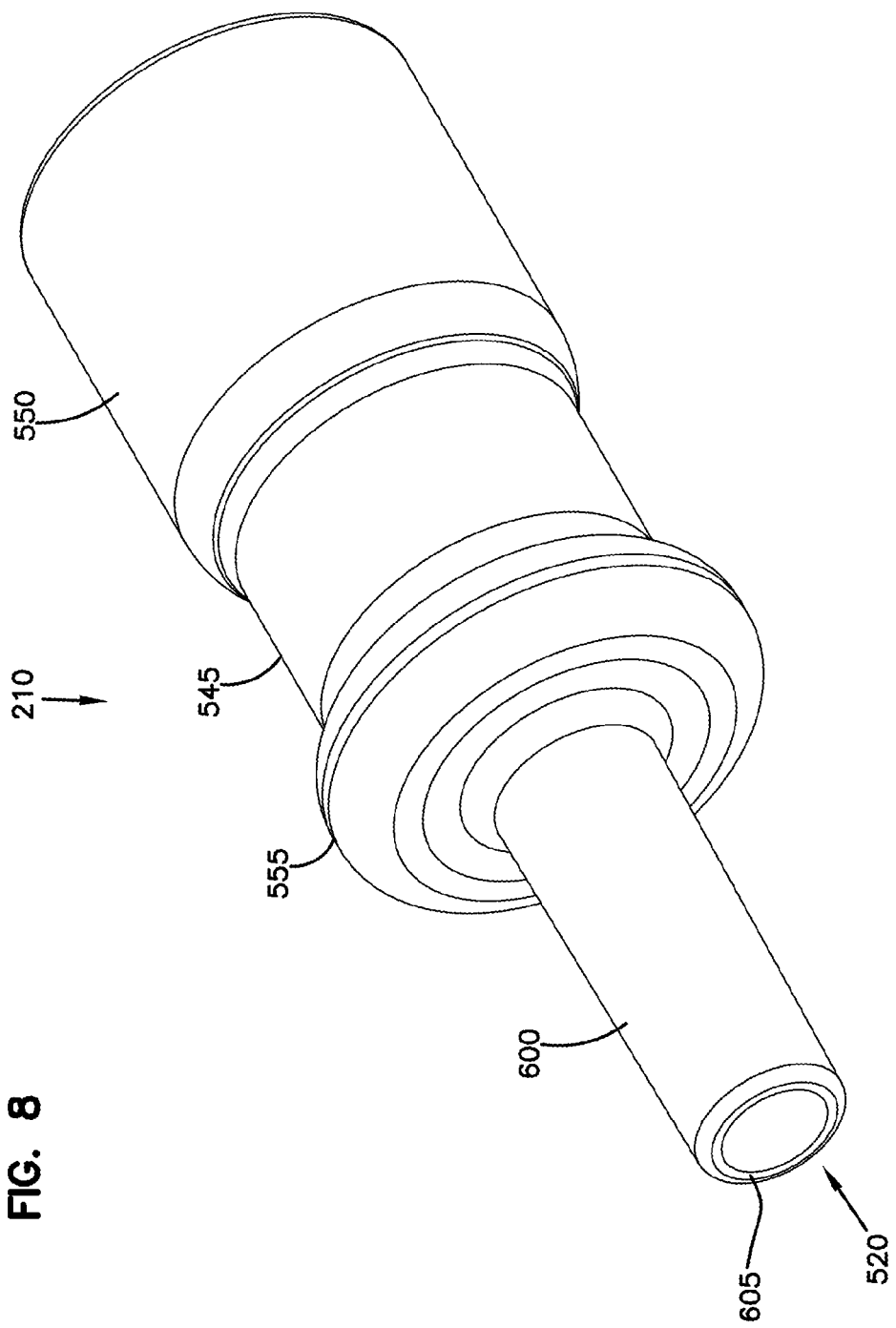
FIG. 8 is another perspective view of the female coupling of FIG. 7.
Figure 9:
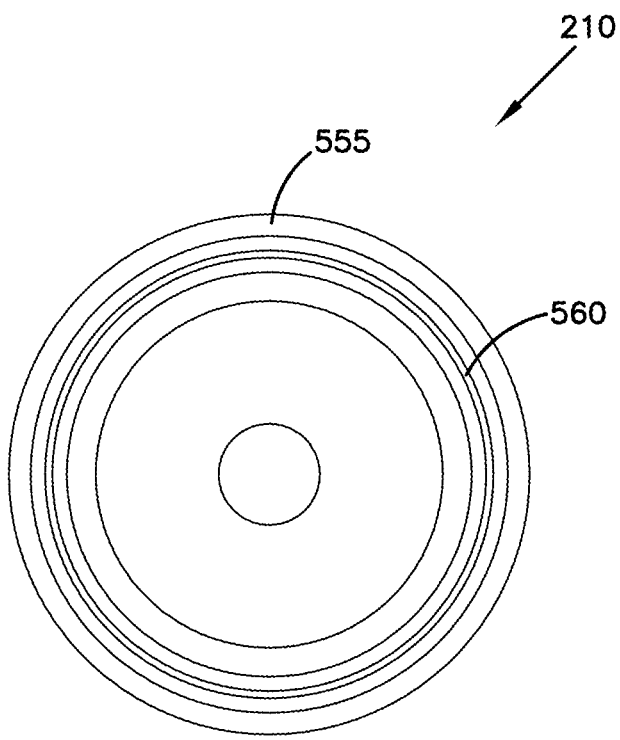
FIG. 9 is an end view of the female coupling of FIG. 7.
Figure 10:
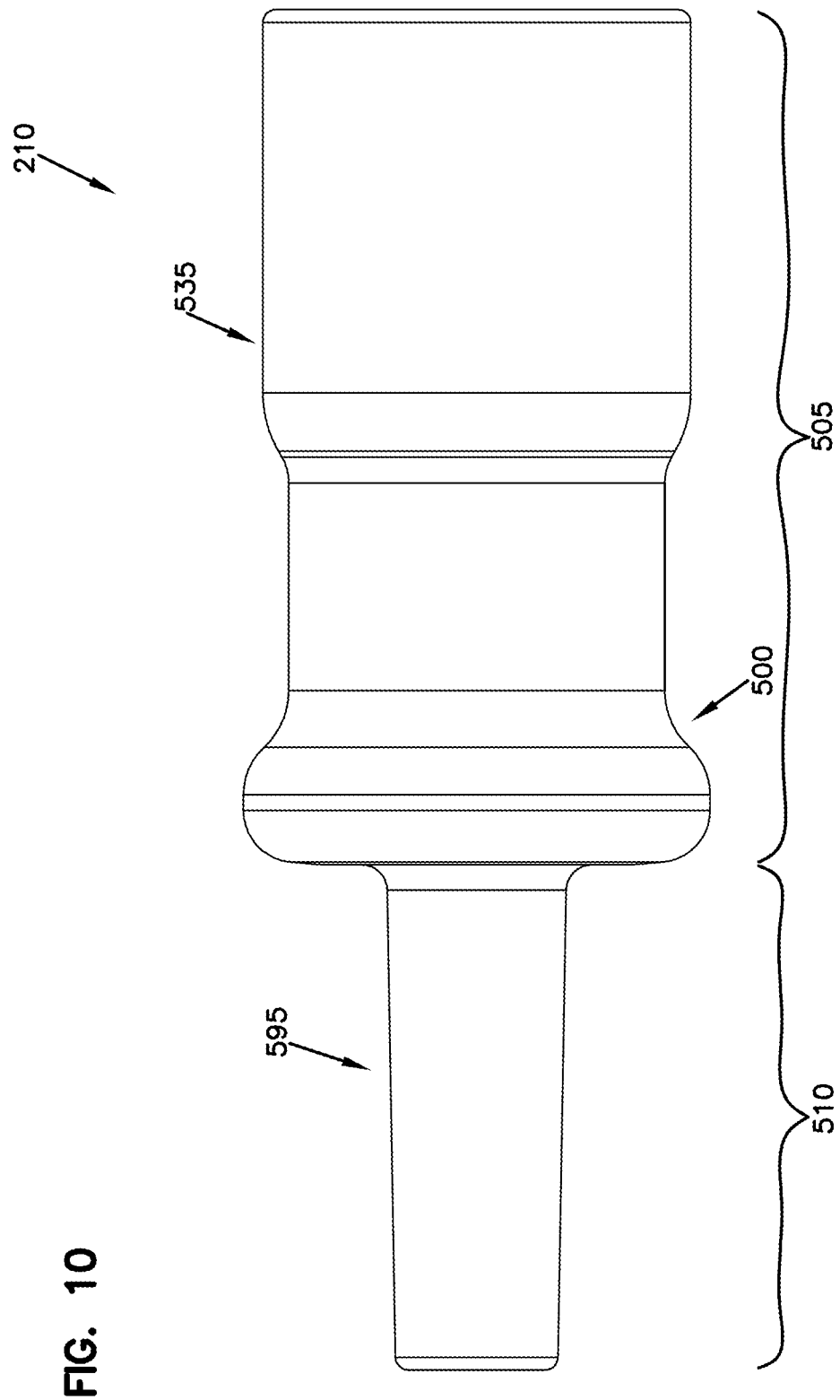
FIG. 10 is a side view of the female coupling of FIG. 7.

Referring now to FIGS. 2-6, the male coupling 205 of the example assembly 200 is shown. In general, the male coupling 205 is radially symmetric. For example, the male coupling 205 is symmetric about a plane X defined as perpendicular to the plane of the male coupling 205 as shown in FIG. 6.

The example male coupling 205 generally includes a body 300 formed as an insert section 305 and a male coupling post section 310. The male coupling 205 further includes a first male coupling aperture 315 and a second male coupling aperture 320 connected by a male coupling internal channel 325.

The insert section 305 includes an insert outer surface 330 defining an insert flange 335, an insert post 340, an insert collar 345, and an insert barb 350. The insert flange 335 includes a first end portion 355 adjacent to the insert post 340, a flared portion 360, and a second end portion 365 adjacent to the male coupling post section 310. In example embodiments, the insert flange 335 generally forms a contoured gripping surface to facilitate coupling and decoupling of the male coupling 205 and the female coupling 210.

The insert post 340 generally includes a plurality of arcuate ribs formed thereon. In the example shown, the insert post 340 includes a first arcuate rib 370 and a diametrically opposed second arcuate rib 375. The first arcuate rib 370 and the second arcuate rib 375 are similar in shape, each including a deformation surface 380, an engagement surface 385, and a retention surface 390. The deformation surface 380 is generally defined approximately at a radial distance R1 measured with respect to the plane X. The engagement surface 385 is generally defined approximately at a radial distance R2 measured with respect to the plane X. An example tangent line L1 of the engagement surface 385 extrapolated to the plane X intersects the plane X at an angle A1. The retention surface 390 is generally defined at a radial distance R3 measured with respect to the plane X. An example tangent line L2 of the retention surface 390 extrapolated to the plane X intersects the plane X at an angle A2.

As described in further detail below in connection with FIGS. 12-19, the first arcuate rib 370 and the second arcuate rib 375 facilitate coupling and decoupling of the male coupling 205 to the female coupling 210. Additionally, geometries of the first arcuate rib 370 and the second arcuate rib 375, such as defined by the angles A1 and A2, and the radial distances R1, R2, and R3, may be selectively defined such that an amount of force required to couple and decouple the male coupling 205 to the female coupling 210 is chosen for a given application.

The insert collar 345 is flanked by the insert post 340 and the insert barb 350. The first male coupling aperture 315 is adjacent to the insert barb 350. The insert collar 345 is generally fitted with an o-ring 395 that interacts with complementary features of the female coupling 210, described further below. The first male coupling aperture 315 is defined by a first insert periphery 400. The first insert periphery 400 is defined at a radial distance R4 measured with respect to the plane X. In example embodiments, the first insert periphery 400 tapers inwardly towards the plane X in a direction of the insert collar 345 to a radial distance R5 as measured with respect to the plane X. The radial distance R5 corresponds to a channel surface 405 of the male coupling internal channel 325.

As mentioned above, the male coupling 205 additionally includes a male coupling post section 310 and a second male coupling aperture 320. The male coupling post section 310 includes a post outer surface 410 defining an elongated post 415 terminated with a post barb 420. However, other embodiments are possible. For example, in some embodiments the post barb 415 is omitted from the elongated post 415 and the elongated post 415 is configured as a tapered stem. Still other embodiments are possible as well. The post barb 420 tapers inwardly towards the plane X from a post barb end surface 425 in a direction of the second male coupling aperture 320. The post barb 420 generally facilitates secure connections to conduits (e.g., first conduit 135) running to various equipment or other applications. The second male coupling aperture 320 is adjacent to the post barb 420 and is defined by a third insert periphery 430. The third insert periphery 430 is defined by the radial distance R5 corresponding to the channel surface 405 of the male coupling internal channel 325.

Figure 11:
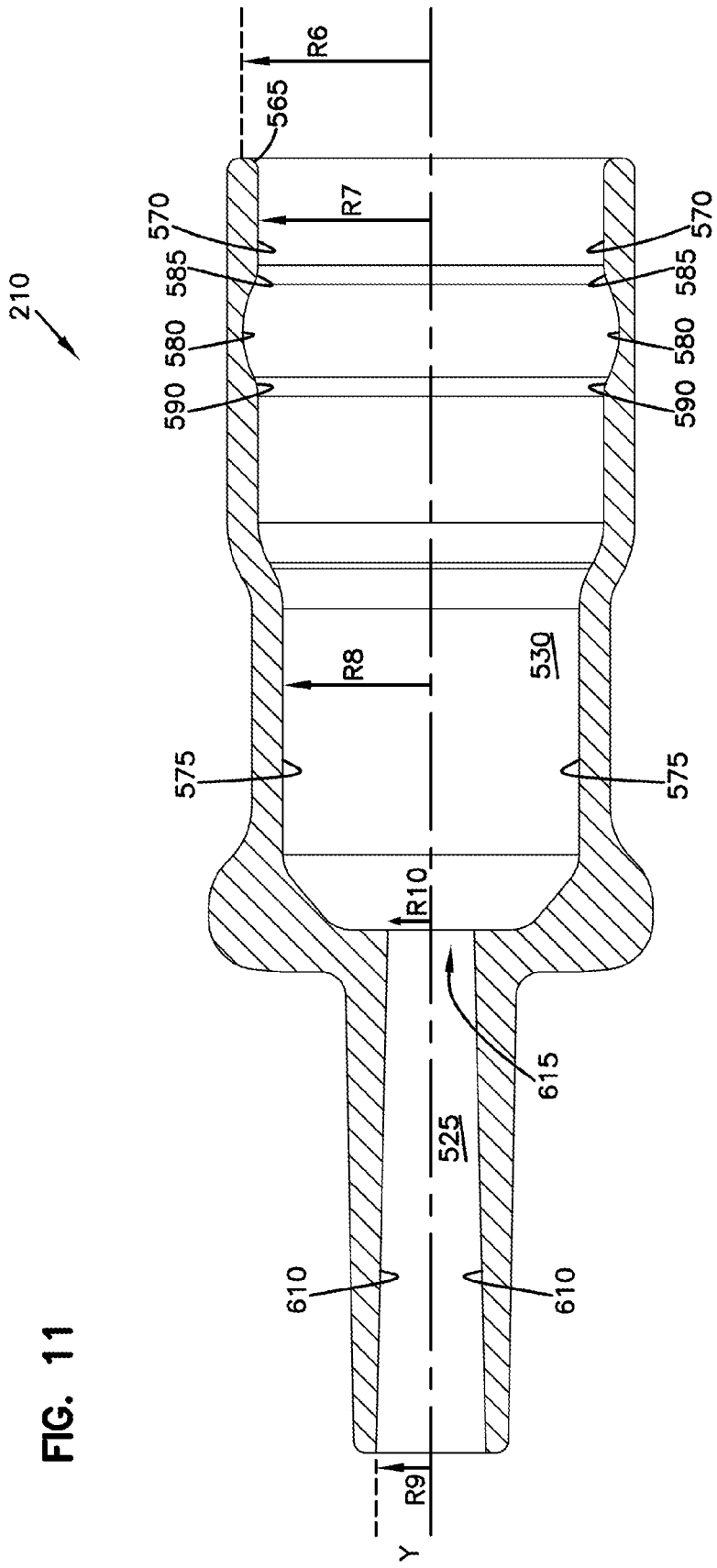
FIG. 11 is a cross-sectional view of the female coupling of FIG. 10.
Figure 12:
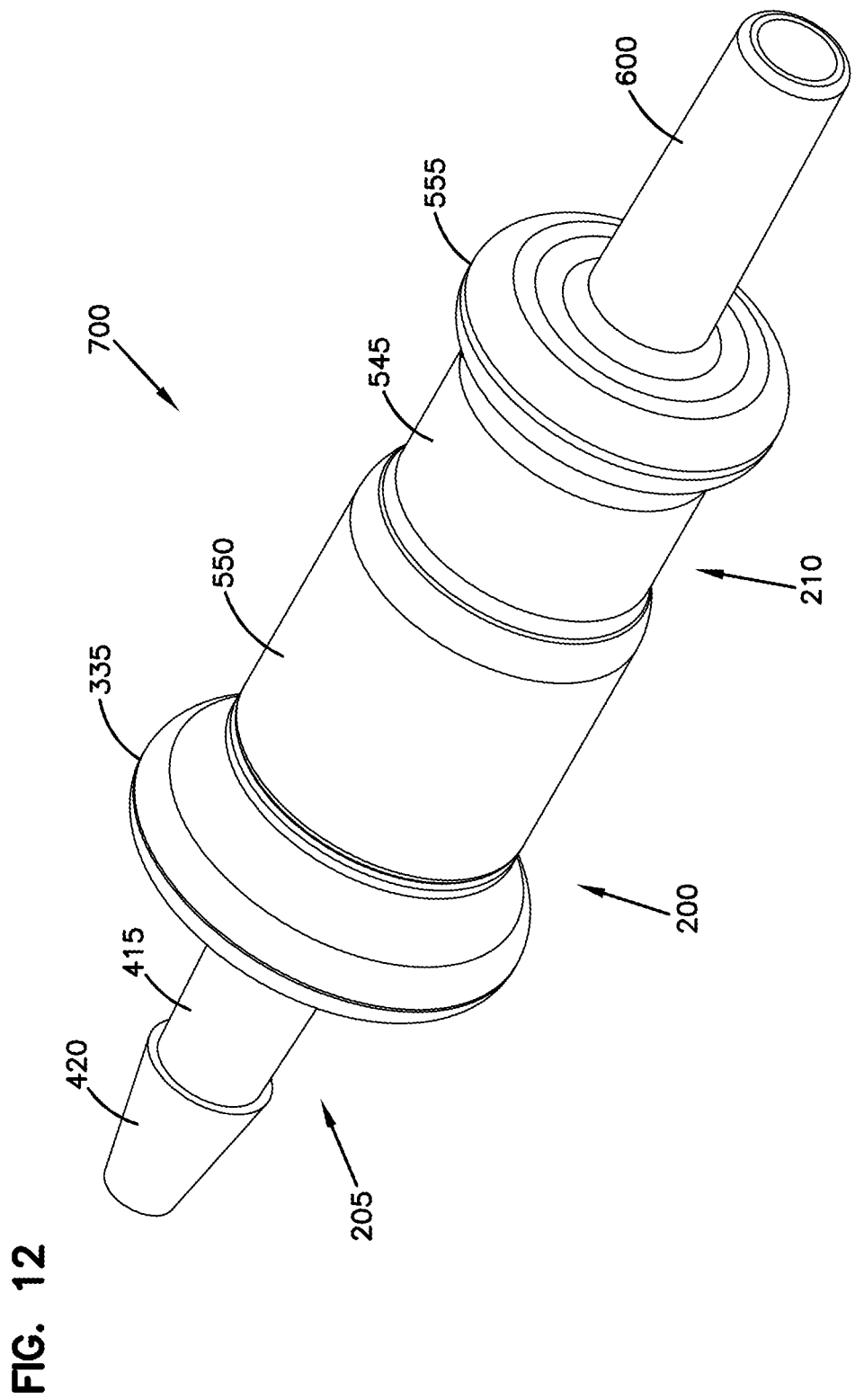
FIG. 12 is a perspective view of the male coupling and female coupling of FIGS. 2-11 in a fully coupled state.
Figure 13:
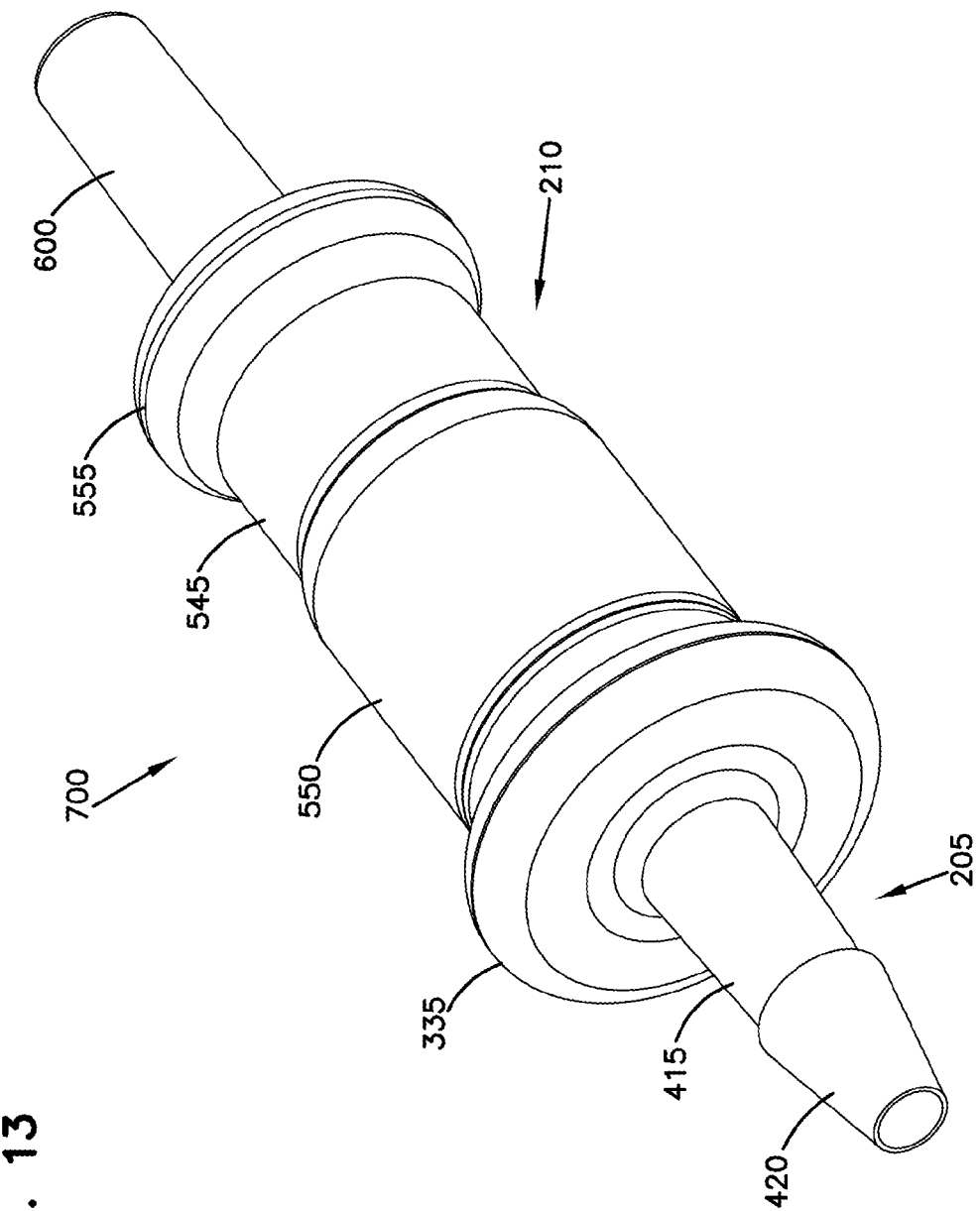
FIG. 13 is another perspective view of the male coupling and female coupling of FIG. 12.
Figure 14:
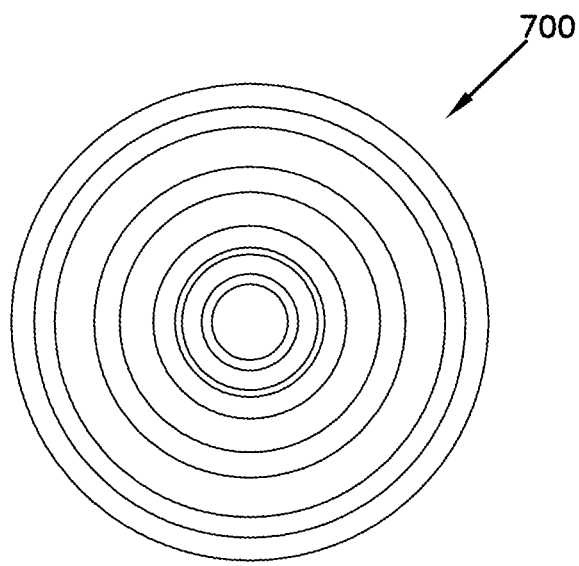
FIG. 14 is an end view of the male coupling and female coupling of FIG. 12.
Figure 15:
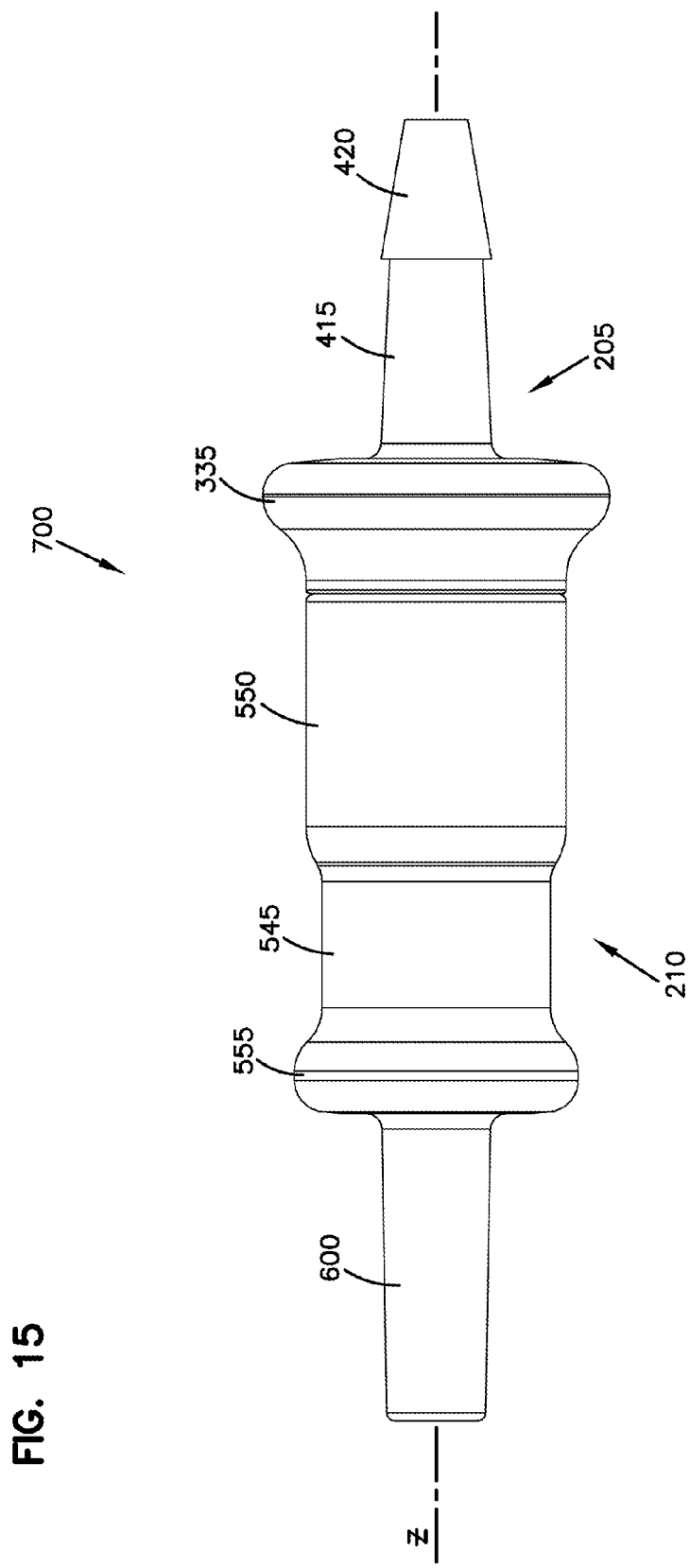
FIG. 15 is a side view of the male coupling and female coupling of FIG. 12.
Figure 16:
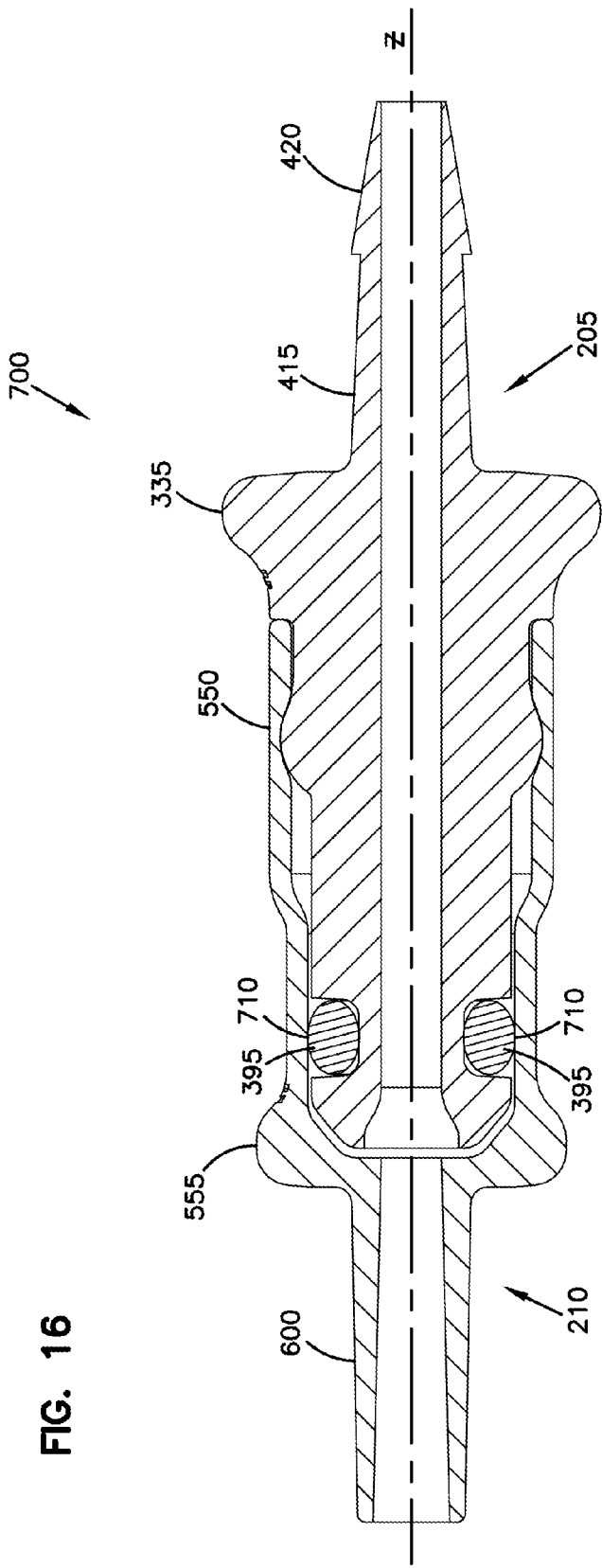
FIG. 16 is a cross-sectional view of the male coupling and female coupling of FIG. 15.

Referring now to FIGS. 7-11, the female coupling 210 of the example assembly 200 is shown. In general, the female coupling 210 is radially symmetric. For example, the female coupling 205 is radially symmetric about an axis Y defined as perpendicular to the plane of the female coupling 250 as shown in FIG. 11.

The female coupling 210 generally includes a body 500 formed as a receptacle section 505 and a female coupling post section 510. The female coupling 210 further includes a first female coupling aperture 515 and a second female coupling aperture 520. The first female coupling aperture 515 and the second female coupling aperture 520 are connected by a female coupling internal channel 525 in fluid connection with an insertion cavity 530 of the female coupling 210.

The receptacle section 505 generally includes a receptacle outer surface 535 and a receptacle inner surface 540. The receptacle outer surface 535 defines a receptacle collar 545 flanked by a first receptacle flange 550 and a second receptacle flange 555. The receptacle collar 545, together with the first receptacle flange 550 and the second receptacle flange 555, provide a contoured gripping surface to facilitate mating of the male coupling 205 to the female coupling 210.

The first female coupling aperture 515 is adjacent to the first receptacle flange 550. The first female coupling aperture 515 is defined by a first receptacle periphery 560 at a radial distance R6 measured with respect to the axis Y. As described further below, the first receptacle periphery 560 is mechanically deformable to a radial distance greater than R6 to facilitate coupling and decoupling of the male coupling 205 to the female coupling 210.

The receptacle inner surface 540 defines the insertion cavity 530 including a curved lead-in surface 565 formed adjacent to the first receptacle periphery 560, a rib engagement surface 570, a sealing surface 575, a rib retention groove 580, and a first retention surface 585, and a first clearance surface 590. The rib engagement surface 570 is generally a flat surface normally defined at a radial distance R7 measured with respect to the axis Y. Similarly, the sealing surface 575 is generally a flat surface normally defined at a radial distance R8 measured with respect to the axis Y. The rib retention groove 580 is flanked by the first retention surface 585 and the first clearance surface 590 and is generally complementary to the geometry of the first arcuate rib 370 and the second arcuate rib 375 of the male coupling 205.

As described in further detail below in connection with FIGS. 12-19, each of the lead-in surface 565, rib engagement surface 570, sealing surface 575, rib retention groove 580, first retention surface 585, and first clearance surface 590 facilitate coupling and decoupling of the male coupling 205 to the female coupling 210.

The female coupling post section 510 of the female coupling 210 includes a post outer surface 595 defining an elongated post 600 extending in a direction outwardly from the receptacle section 505 along the axis Y and terminating at the second female coupling aperture 520. However, other embodiments are possible as well. For example, the elongated post 600 may be terminated in any of a plurality of desired terminations, such as a post barb or other termination. The second female coupling aperture 520 is defined by a second receptacle periphery 605 defined at a radial distance R9 with respect to axis Y. The second receptacle periphery 605 corresponds to a channel surface 610 of the female coupling internal channel 525. In example embodiments, the channel surface 610 tapers inwardly towards the axis Y in a direction of the insertion cavity 530 to a third female coupling aperture 615 defined at a radial distance R10 as measured with respect to the axis Y. The female coupling internal channel 525 is in fluid connection with the insertion cavity 530 at the third female coupling aperture 615.

Figure 17:
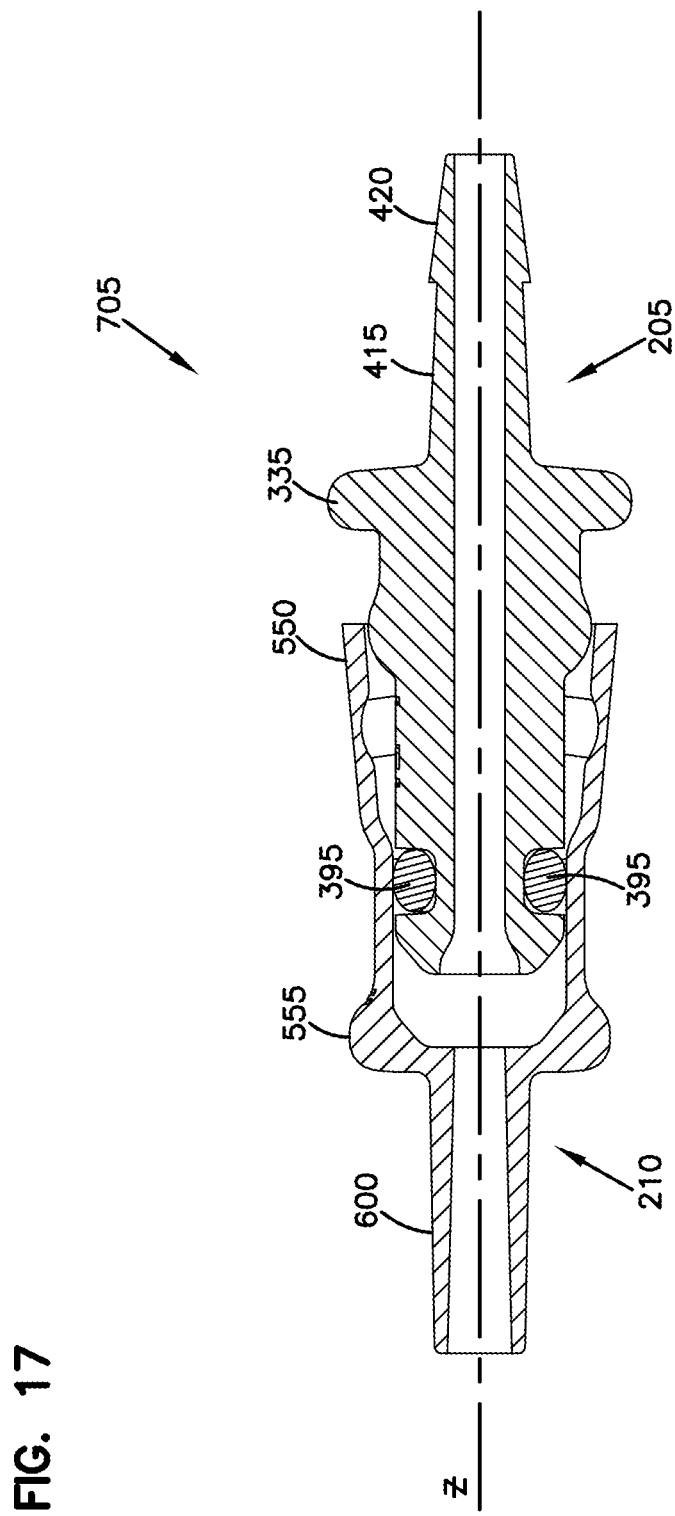
FIG. 17 is a cross-sectional view of the male coupling and female coupling of FIGS. 2-11 in a partially coupled state.
Figure 18:
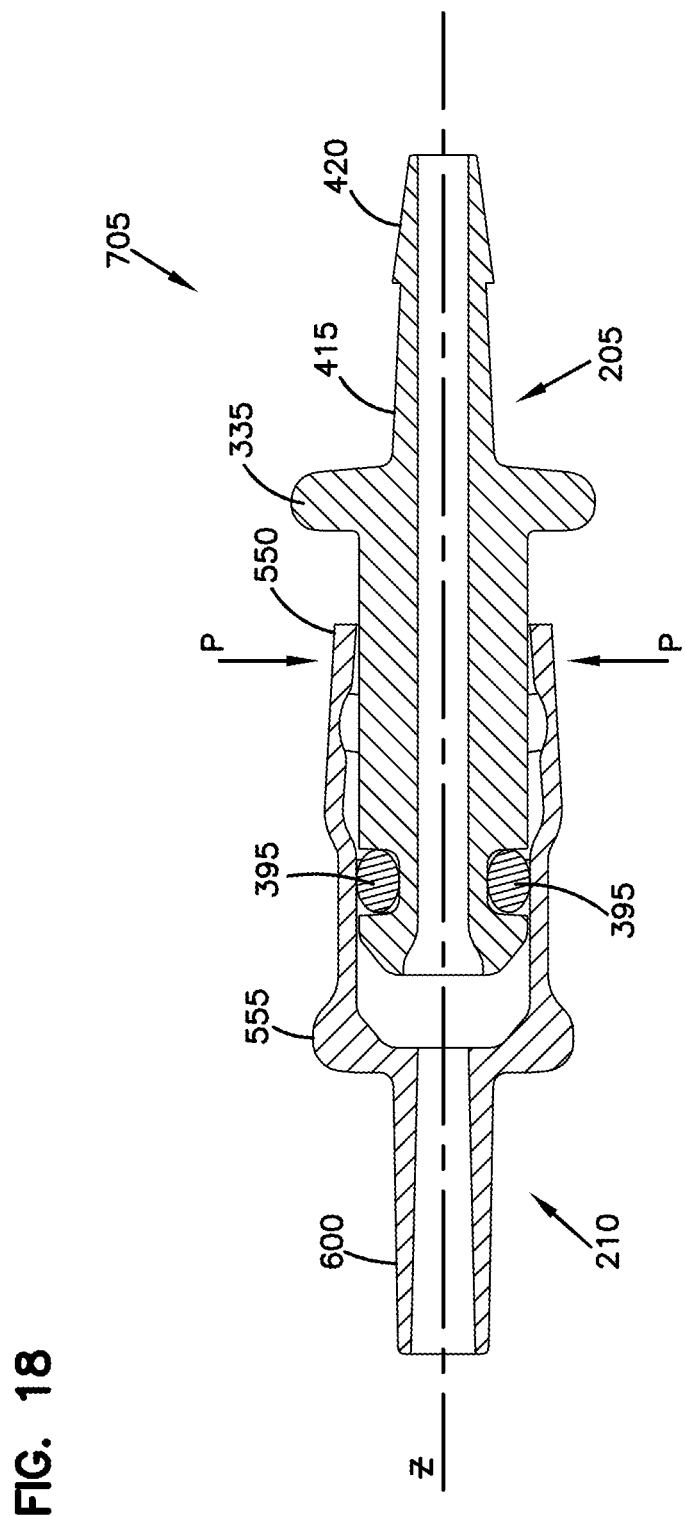
FIG. 18 is another cross-sectional view of the male coupling and female coupling of FIGS. 2-11 in a partially coupled state.
Figure 19:
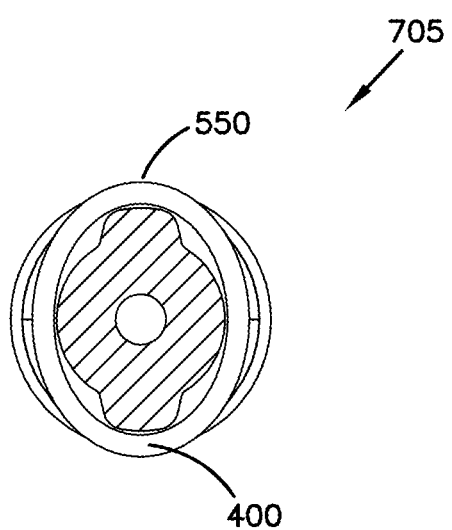
FIG. 19 is a cross-sectional end view of the male coupling and female coupling of FIG. 18.
Figure 20:
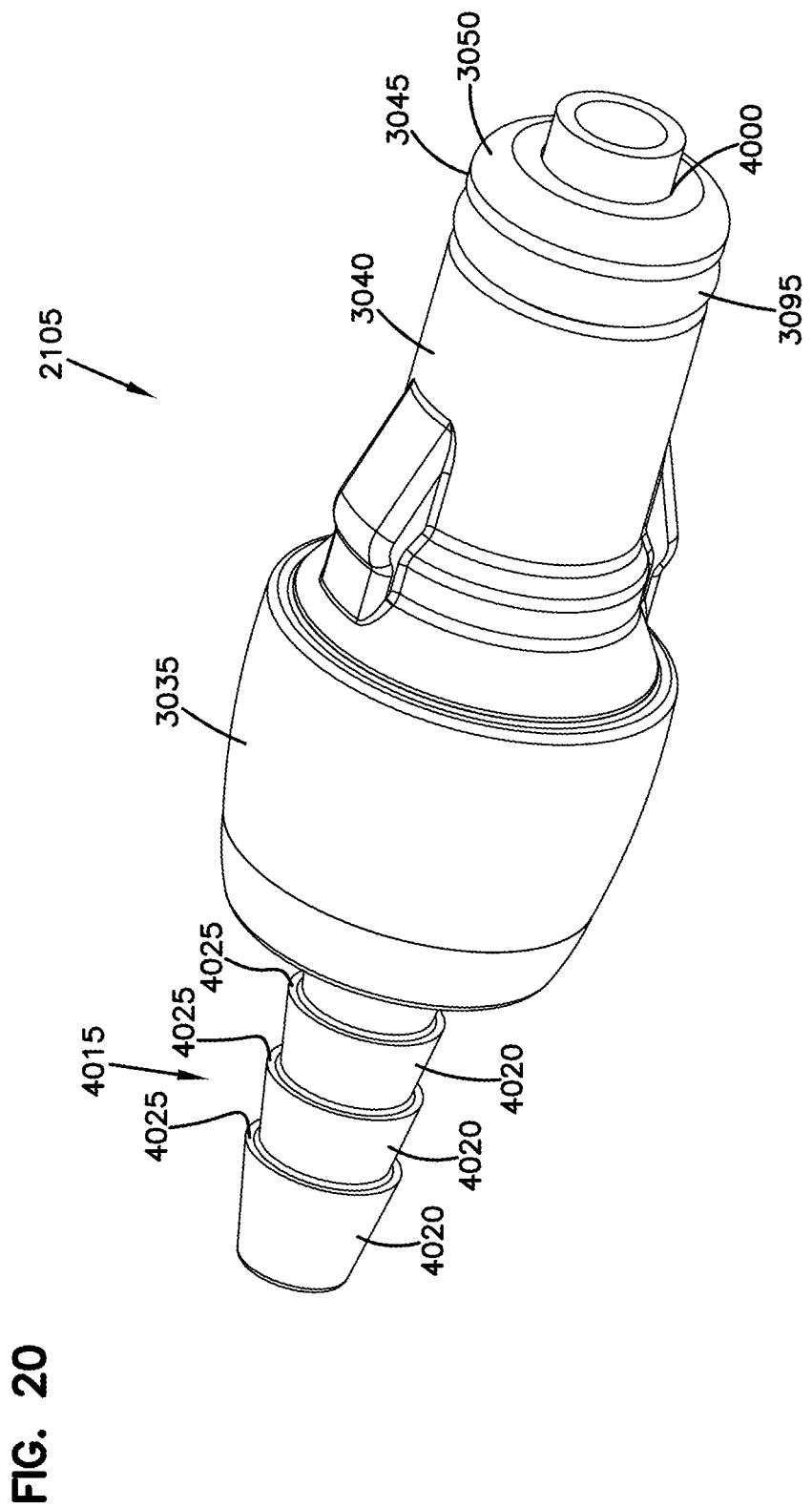
FIG. 20 is a perspective view of another example male coupling.
Figure 21:
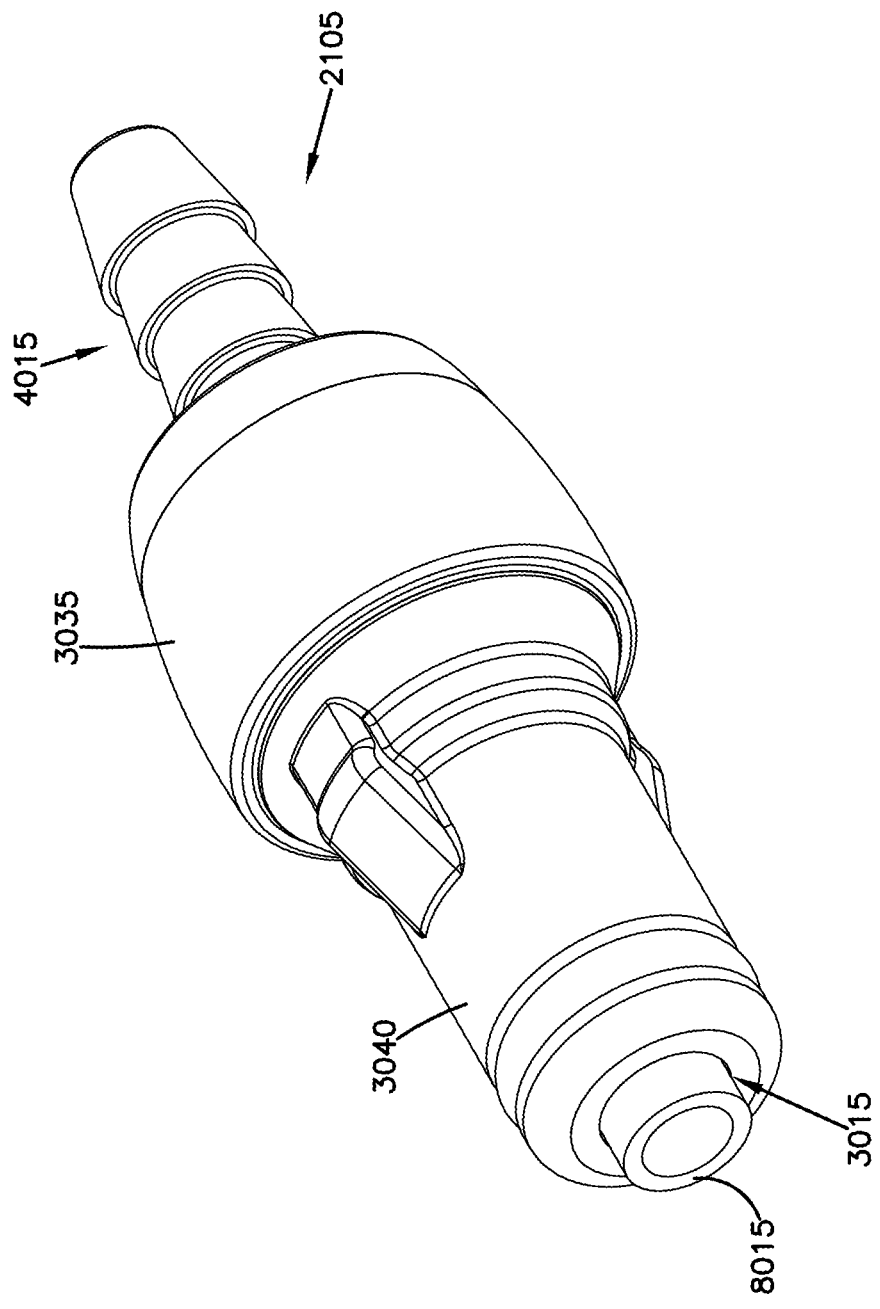
FIG. 21 is another perspective view of the male coupling of FIG. 20.

Referring now to FIGS. 12-19, the male coupling 205 and female coupling 210 of the example assembly 200 are shown in fully coupled state 700 (FIGS. 12-16) and a partially coupled state 705 (FIGS. 17-19). The male coupling 205 and the female coupling 210 are aligned about a longitudinal axis Z.

Referring to FIGS. 17-19, the male coupling 205 and female coupling 210 of the example assembly 200 are coupled via a push-to-connect process to form a fluid tight pressure seal. As noted above, both the male coupling 205 and female coupling 210 do not require a specific radial orientation when the male coupling 205 is coupled to the female coupling 210. Additionally, in example embodiments, the male coupling 205 and female coupling 210 are non-keyed. In this manner, the male coupling 205 may be inserted into the female coupling 210 in any radial orientation.

The male coupling 205 is coupled to the female coupling 210 by orientating the male coupling 205 such that the insert post 340 is pointing towards and inserted through the first female coupling aperture 515 and into the insertion cavity 530.

This motion proceeds with minimal resistance until the engagement surfaces 385 of the first arcuate rib 370 and the second arcuate rib 375 contact the lead-in surface 565 of the female coupling 210. An initial application of force along the axis Z is required for further insertion of the insert post 340 into insertion cavity 530. Upon application of sufficient force, interaction of the engagement surface 385 with the lead-in surface 565 deforms the first receptacle periphery 560 from a normally circular shape into an elliptical shape (e.g., see FIG. 19). The o-ring 395 interacts with the sealing surface 575 of the female coupling 210 to form a fluid seal 710.

Figure 4:
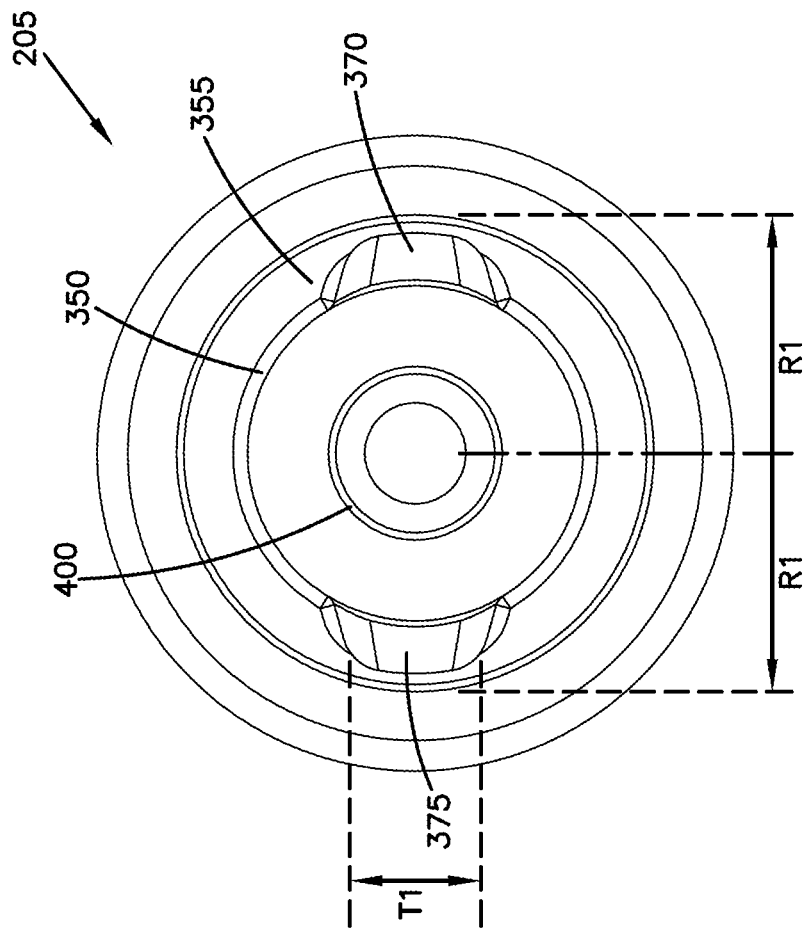
FIG. 4 is an end view of the male coupling of FIG. 2.
Figure 5:
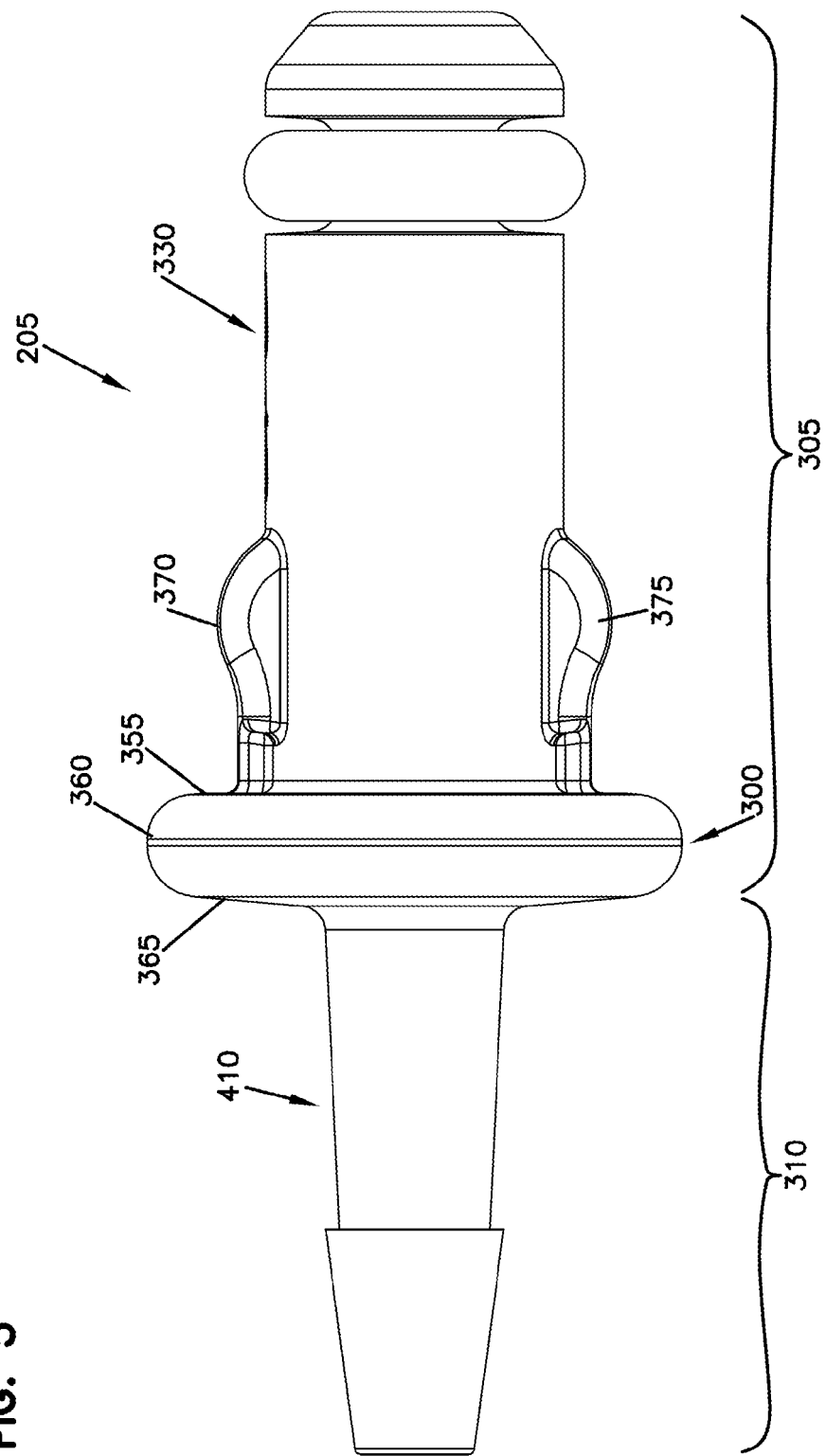
FIG. 5 is a side view of the male coupling of FIG. 2.

In example embodiments, a magnitude of force required to deform the first receptacle periphery 560 from a normally circular shape into an elliptical shape via forced engagement with the first arcuate rib 370 and the second arcuate rib 375 is a function of material and structural properties of the receptacle section 505 of the female coupling 210, slope of the tangent line L1 of the engagement surface 385, and the radial distance R1 of the example deformation surface 380 as defined above. As shown in FIG. 4, twice the radial distance R1 corresponds to a maximum distance or width between the first arcuate rib 370 and the second arcuate rib 375.

For example, a greater force would be required to deform the first receptacle periphery 560 from a normally circular shape into an elliptical shape if the tangent line L1 of the engagement surface 385 corresponds to an angle of 60 degrees in comparison to an angle of 30 degrees. In the example, a 60 degree slope of the engagement surface 385 would present a greater insertion resistance than a 30 degree slope. Additionally, a greater force would be required to deform the first receptacle periphery 560 from a normally circular shape into an elliptical shape in proportion to a magnitude of the radial distance R1, as described further below.

The deformation surface 380 of the first arcuate rib 370 and the second arcuate rib 375 contacts the rib engagement surface 570 of the female coupling 210 upon further application of force along the axis Z. In the example embodiment, the deformation surface 380 imparts an increasing load on the receptacle section 505 in a direction normal and outward with respect to the axis Z as the insert post 340 is further inserted into the insertion cavity 530. An increased application of force is required to further position the insert post 340 into the first female coupling aperture 515 based on the magnitude of the radial distance R1.

For example, a greater force would be required to further position the insert post 340 into the insertion cavity 530 if the radial distance R1 is defined as 10 length units in comparison to a radial distance R1 defined as 5 length units. In the example, a radial distance R1 of 10 length units would require a more severe elliptical distortion, and thus a greater applied force to further position the insert post 340 into the first female coupling aperture 515, of the first receptacle periphery 560 than a radial distance R1 defined as 5 length units.

A width T1 of the first arcuate rib 370 and the second arcuate rib 375 can be varied to change the force necessary to couple and uncouple the male coupling 205 from the female coupling 210. For example, the width T1 can be increased to increase the force, and decreased to decrease the force.

The deformation surface 380 of the first arcuate rib 370 and the second arcuate rib 375 contact the rib engagement surface 570 of the female coupling 210 upon further application of force along the axis Z until the retention surface 390 of the first arcuate rib 370 and the second arcuate rib 375 engage with the first retention surface 585 of the female coupling 210. Upon engagement of the retention surface 390 with the first retention surface 585, the first arcuate rib 370 and the second arcuate rib 375 are forcefully drawn into the rib retention groove 580 of the female coupling 210 in a snap-action by virtue of rearrangement of load imparted on the receptacle section 505 by the first arcuate rib 370 and the second arcuate rib 375 into force components both normal and coincident to the axis Z.

Upon the first arcuate rib 370 and the second arcuate rib 375 being snapped into the rib retention groove 580, the first receptacle periphery 560 revert approximately to the normally circular state and the male coupling 205 and female coupling 210 are in the fully coupled state 700, as shown in FIGS. 12-16.

In example embodiments, the male coupling 205 is decoupled from the female coupling 210 via application of a pinching force to the first receptacle flange 550 to deform the first receptacle periphery 560 into an elliptical, release shape or by simply pulling the male coupling 205 and female coupling 210 in opposite directions with enough force. Subsequently, while maintaining the applied force to first receptacle flange 550, the insert post 340 of the male coupling 205 is removed from the female coupling 210.

For example, referring specifically to FIGS. 17 and 18, a pinching force P may applied to the first receptacle flange 550 at positions located between the first arcuate rib 370 and the second arcuate rib 375 to deform the first receptacle periphery 560 into the elliptical shape. While maintaining the applied pinching force P to first receptacle flange 550, the insert post 340 of the male coupling 205 is removed from the female coupling 210 by pulling the male coupling 205 away from the female coupling 210 in a direction along the axis Z. As the male coupling 205 is pulled away from the female coupling 210 the first receptacle periphery 560 is deformed to an elliptical shape of similar eccentricity to the elliptical shape assumed by the first receptacle periphery 560 when the male coupling 205 is coupled to the female coupling 210 as described above.

In example embodiments, a magnitude of force required to deform the first receptacle periphery 560 from a normally circular shape into an elliptical shape via application of a pinching force, followed by disconnection of the male coupling 205 from the female coupling 210 is a function of material and structural properties of the receptacle section 505 of the female coupling 210, slope of the tangent line L2 of the retention surface 390, and the radial distance R1 corresponding to the example deformation surface 380.

For example, a greater force would be required to deform the first receptacle periphery 560 from a normally circular shape into an elliptical shape and disconnect the male coupling 205 from the female coupling 210 if the tangent line L2 of the retention surface 390 corresponds to an angle of 60 degrees in comparison to an angle of 30 degrees. In the example, a 60 degree slope of the retention surface 390 would be present a greater pulling resistance than a 30 degree slope. Additionally, a greater force would be required to deform the first receptacle periphery 560 from a normally circular shape into an elliptical shape in proportion to a magnitude of the radial distance R1, which corresponds to a maximum distance or width between the first arcuate rib 370 and the second arcuate rib 375 as described above. Further, as noted above, the width T1 of the ribs 370, 375 can be varied to increase and decrease coupling force.

FIGS. 20-40 illustrate a second example breakaway coupling assembly 2000 according to the principles of the present disclosure. The example assembly 2000 is a valved coupling assembly including a male coupling 2105 and a female coupling 2110.

In general, the male coupling 2105 and the female coupling 2110 of the example assembly 2000 are similar to the male coupling 205 and the female coupling 210 of the example assembly 200 described above with respect to FIG. 1-19, except for the differences noted below.

Referring now to FIGS. 20-26, the male coupling 2105 of the example assembly 2000 is shown. The male coupling 2105 is radially symmetric about a longitudinal axis T and includes an insert section 3005, a male coupling post section 3010, a first male coupling aperture 3015, a second male coupling aperture 3020. The insert section 3005 includes an insert outer surface 3030 defining an insert flange 3035, an insert post 3040, an insert collar 3045, and an insert barb 3050. The insert flange 3035 includes a first end portion 3055 adjacent to the insert post 3040, a bulbous portion 3060, and a second end portion 3065 adjacent to the male coupling post section 3010. In example embodiments, the insert flange 3035 forms a contoured gripping surface to facilitate coupling and decoupling of the male coupling 2105 and the female coupling 2110.

Figure 22:
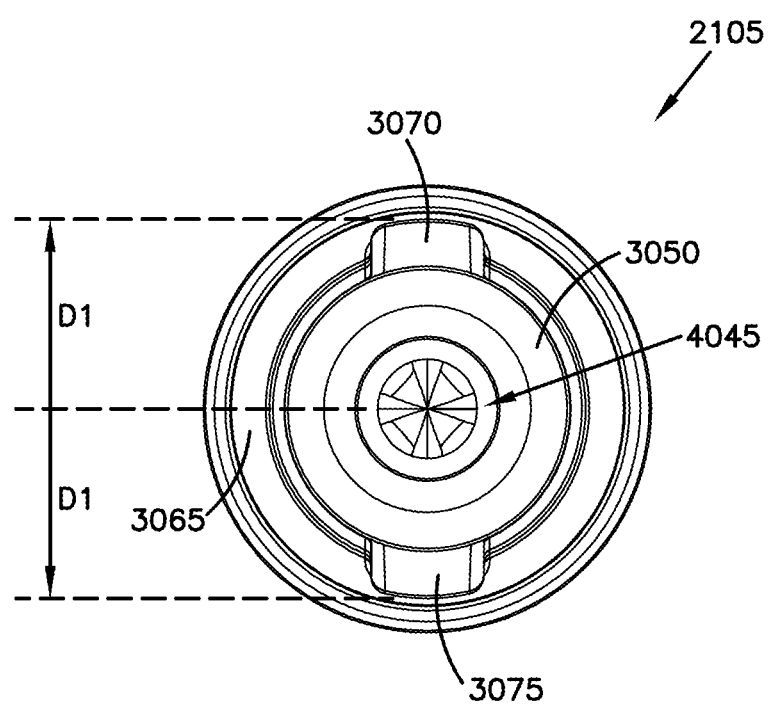
FIG. 22 is an end view of the male coupling of FIG. 20.
Figure 23:
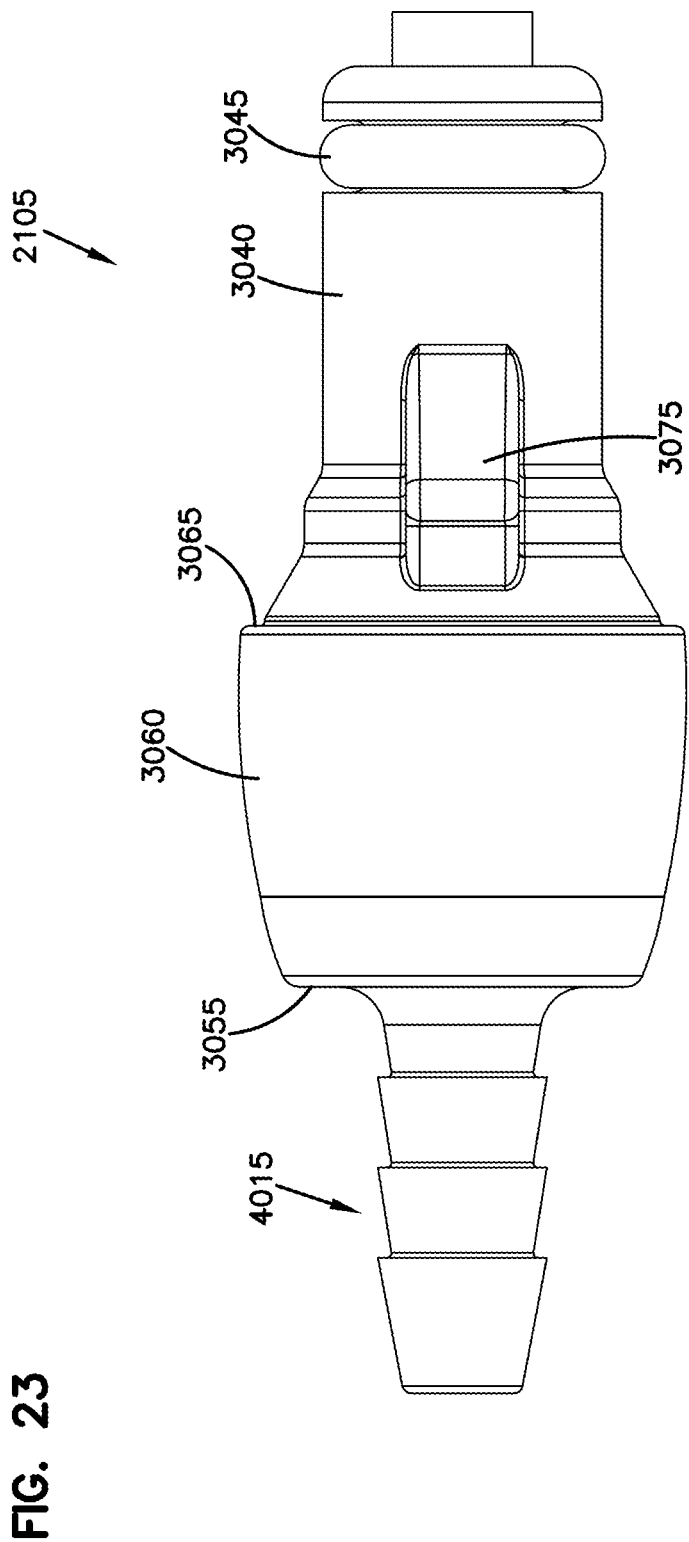
FIG. 23 is another side view of the male coupling of FIG. 20.
Figure 24:
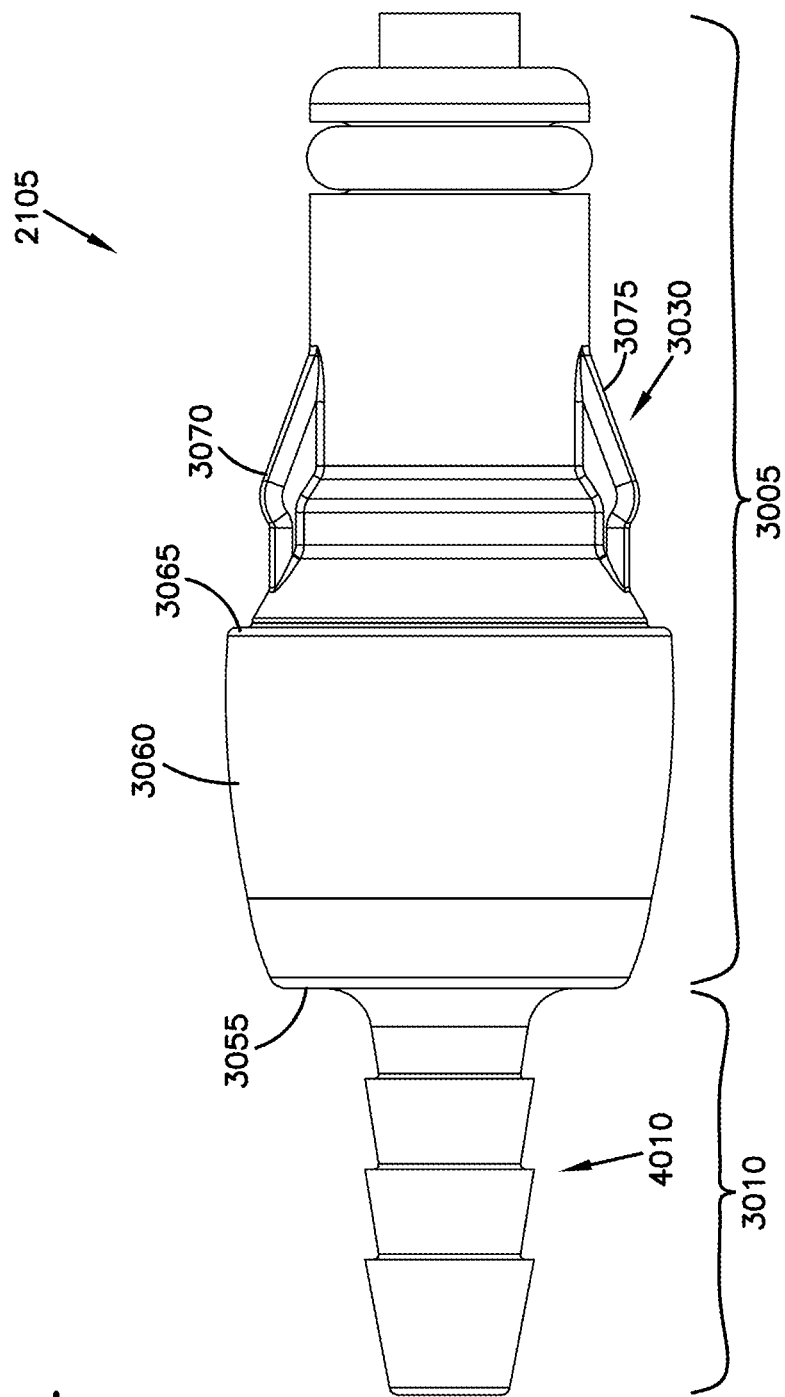
FIG. 24 is a side view of the male coupling of FIG. 20.

The insert post 3040 generally includes a plurality of arcuate ribs formed thereon. In the example shown, the insert post 3040 includes a first arcuate rib 3070 and a diametrically opposed second arcuate rib 3075. The first arcuate rib 3070 and the second arcuate rib 3075 are similar in shape each including a deformation surface 3080, a rib engagement surface 3085, and a retention surface 3090. The deformation surface 3080 is generally defined approximately at a radial distance D1 measured with respect to the axis T. As shown in FIG. 22, twice the radial distance D1 corresponds to a maximum distance or width between the first arcuate rib 3070 and the second arcuate rib 3075. The rib engagement surface 3085 is generally defined approximately at a radial distance D2 measured with respect to the axis T. An example tangent line M1 of the rib engagement surface 3085 extrapolated to the axis T intersects the axis T at an angle B1. The retention surface 3090 is generally defined at a radial distance D3 measured with respect to the axis T. An example tangent line M2 of the retention surface 3090 can be extrapolated to intersect the axis T at an angle B2.

The insert collar 3045 is flanked by the insert post 3040 and the insert barb 3050. The first male coupling aperture 3015 is adjacent to the insert barb 3050. The insert collar 3045 is generally fitted with an o-ring 3095 that interacts with complementary features of the female coupling 2110. The first male coupling aperture 3015 is defined by a first insert periphery 4000. The first insert periphery 4000 is defined at a radial distance D4 measured with respect to the axis T. In example embodiments, the radial distance D4 corresponds to a first channel surface 4005 of a first male coupling internal channel 3025.

The male coupling post section 3010 includes a post outer surface 4010 defining an elongated barbed post 4015 comprising a plurality of post barbs 4020. Each respective post barb 4020 tapers inwardly towards the axis T from a post barb end surface 4025 in a direction of the second male coupling aperture 3020. The post barb 4020 facilitates secure connections to conduits (e.g., first conduit 135) running to various equipment or other applications. However, other embodiments are possible as well. For example, in some embodiments the barbed post 4015 is omitted from the male coupling post section 3010 and the male coupling post section 3010 is terminated in any manner as desired, such as a single barb, a tapered stem, and others. Still other embodiments are possible as well. The second male coupling aperture 3020 is adjacent to the barbed post 4015 and is defined by a second insert periphery 4030. The second insert periphery 4030 is defined by the radial distance D5 corresponding to a second channel surface 4035 of a second male coupling internal channel 4040.

Figure 25:
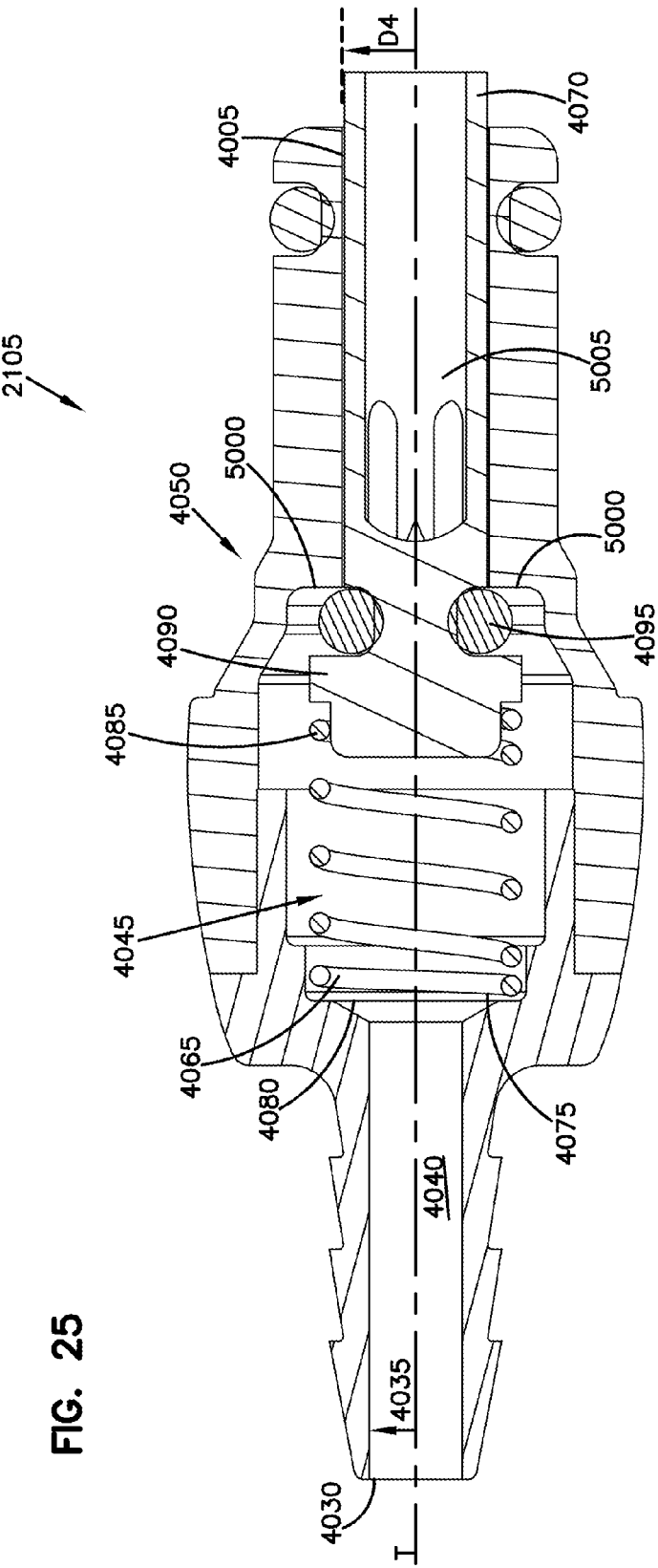
FIG. 25 is a cross-sectional view of the male coupling of FIG. 24.
Figure 26:
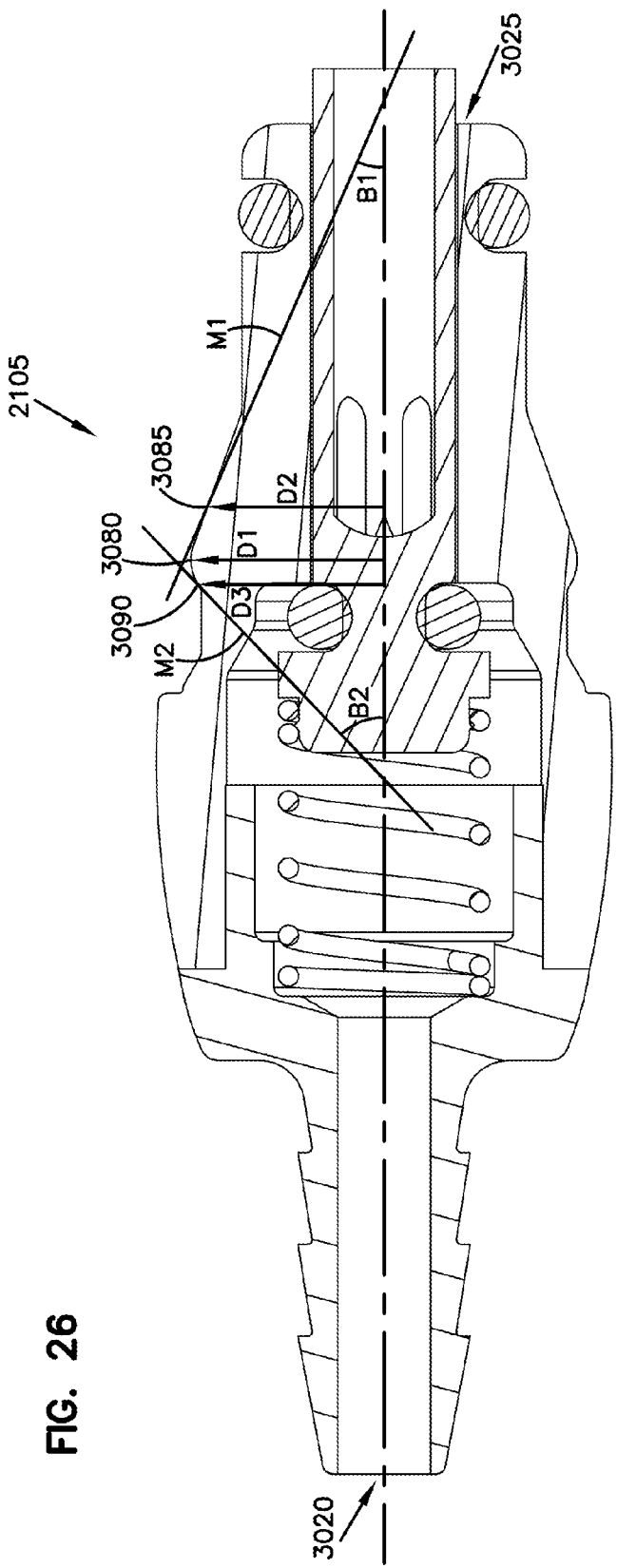
FIG. 26 is another cross-sectional view of the male coupling of FIG. 24.
Figure 27:
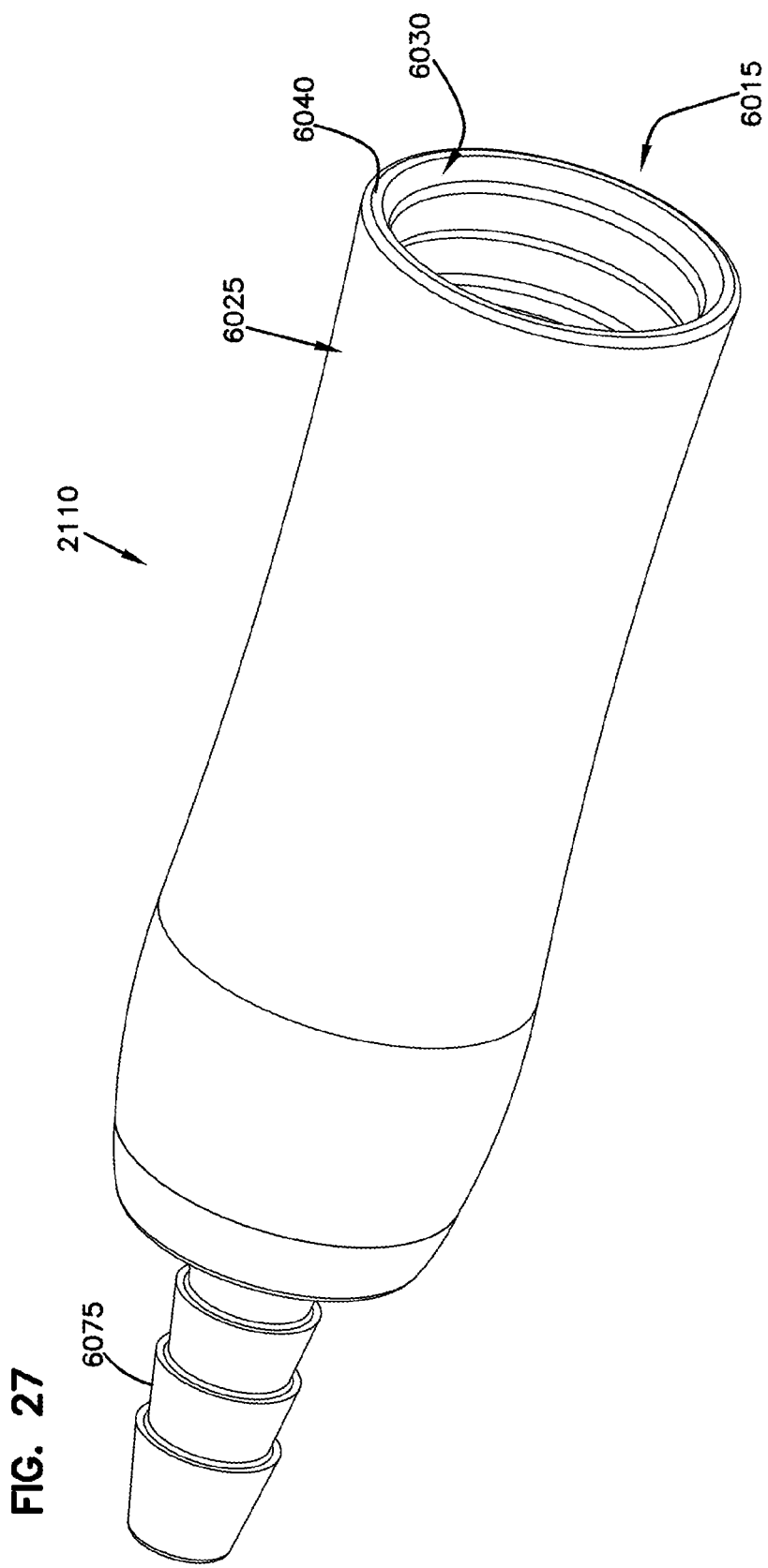
FIG. 27 is a perspective view of another example female coupling.
Figure 28:
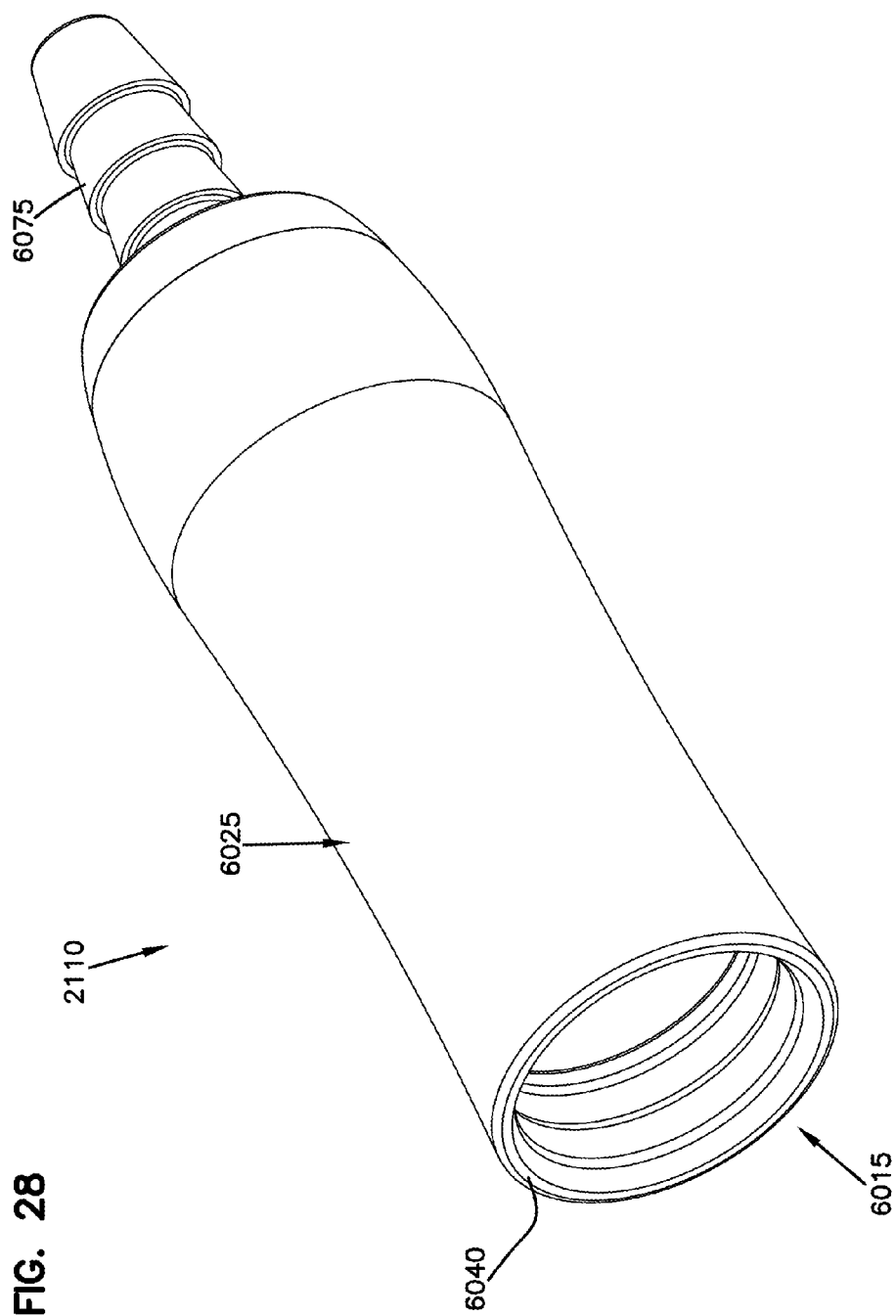
FIG. 28 is a perspective view of the female coupling of FIG. 27.
Figure 29:
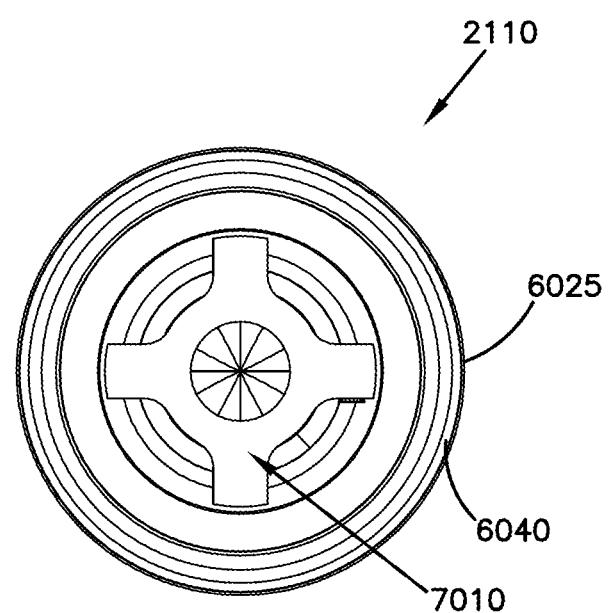
FIG. 29 is an end view of the female coupling of FIG. 27.
Figure 30:
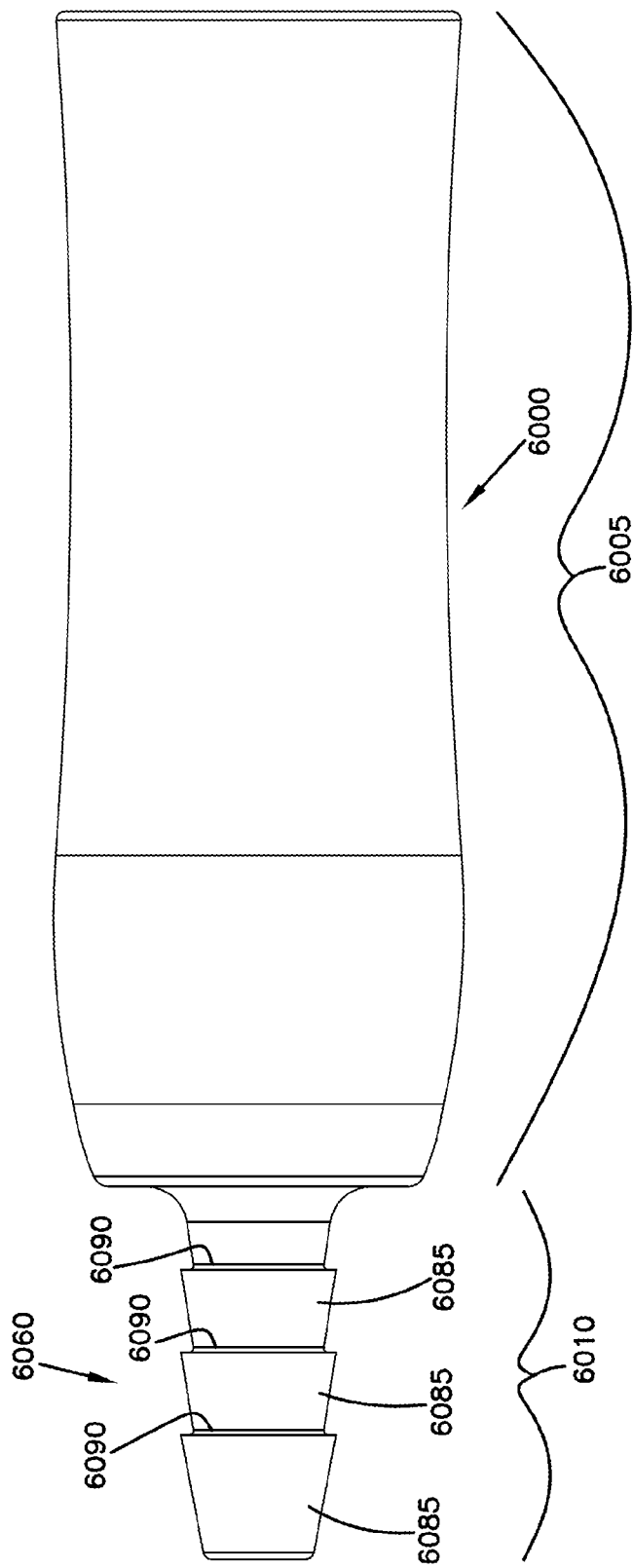
FIG. 30 is a side view of the female coupling of FIG. 27.
Figure 33:
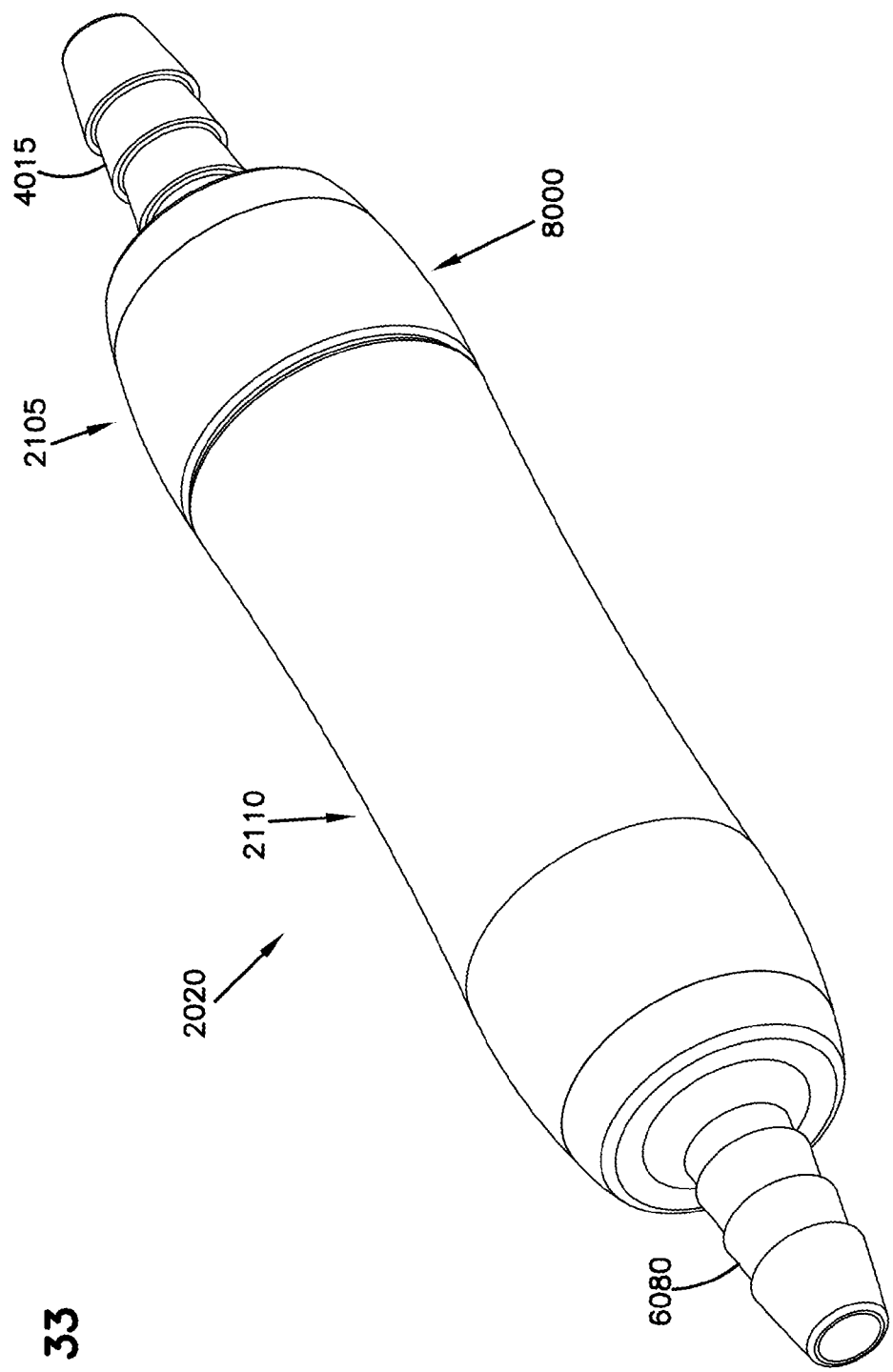
FIG. 33 is another perspective view of the male coupling and female coupling of FIG. 32.
Figure 38:
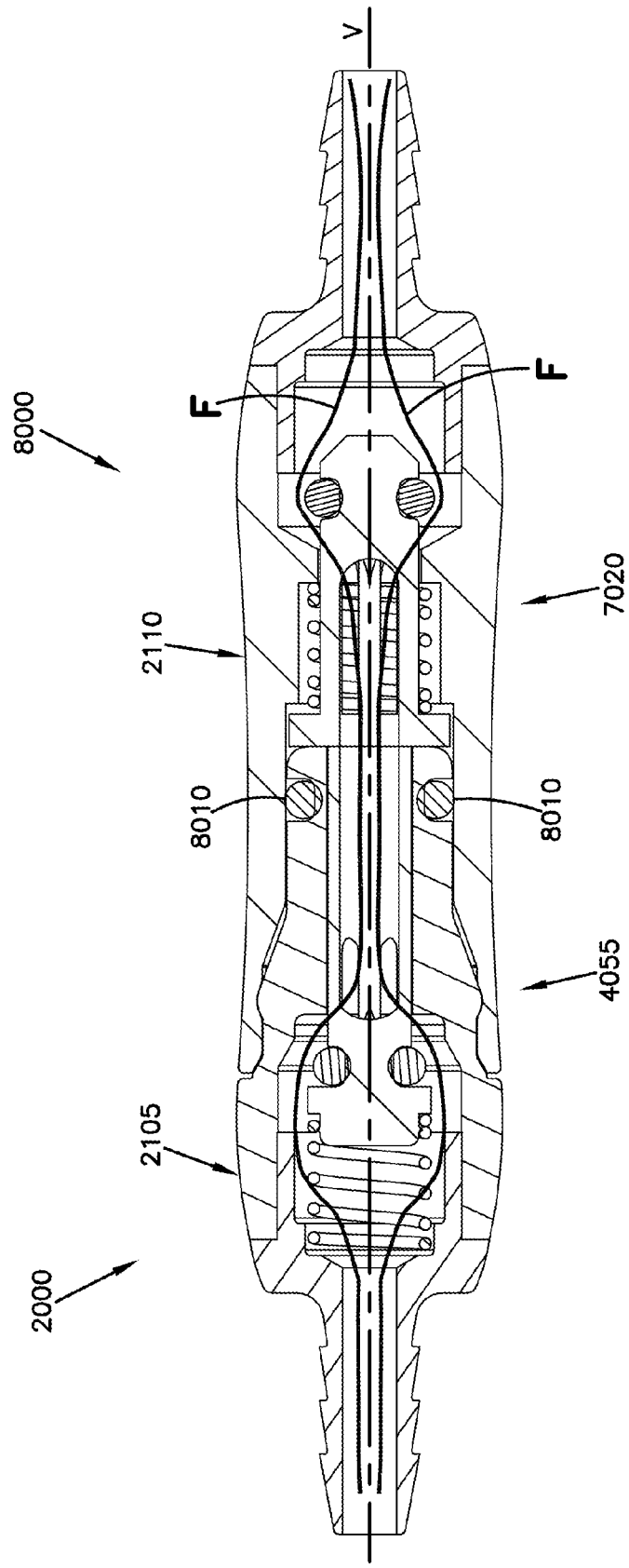
FIG. 38 is a cross-sectional view of the example male coupling and female coupling of FIGS. 20-31 in a fully coupled state.
Figure 39:
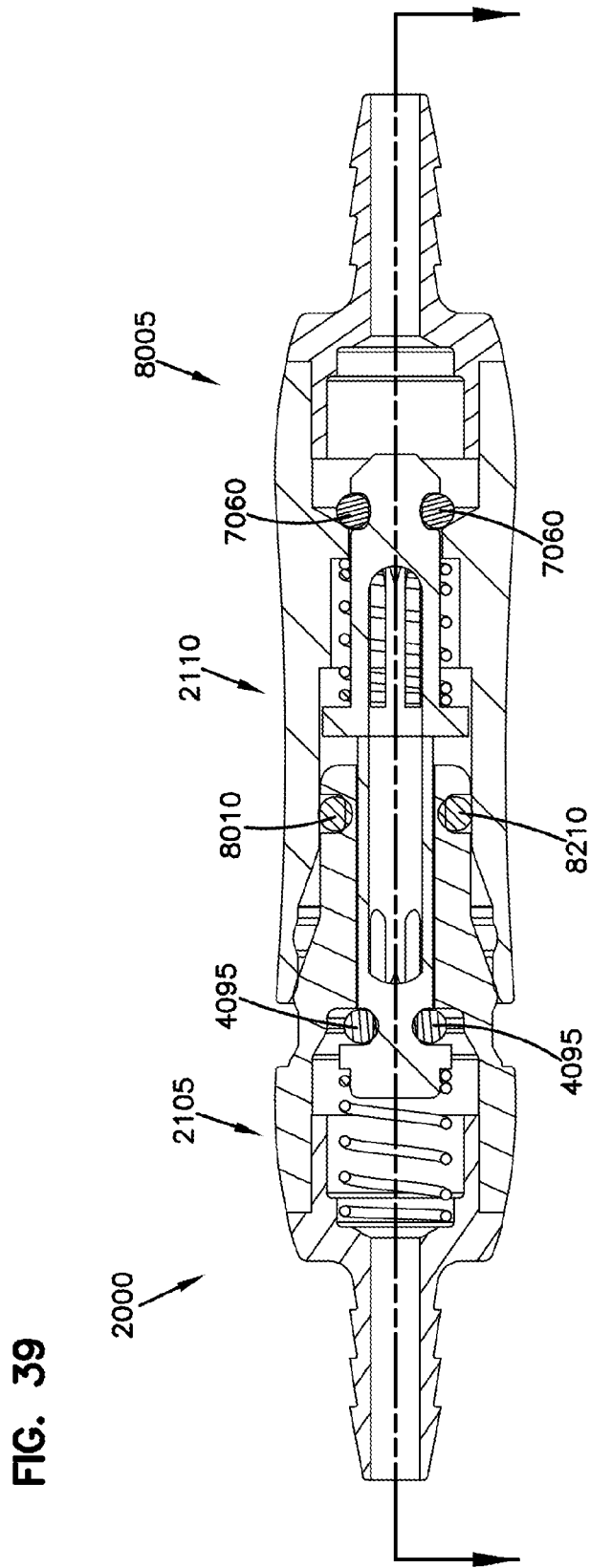
FIG. 39 is a cross-sectional view of the example male coupling and female coupling of FIGS. 20-31 in a partially coupled state.

As mentioned above, the example assembly 2000 is a valved assembly. In example embodiments, the male coupling 2105 includes a male coupling member 4045 that is actuated between a normally closed position 4050 (e.g., as shown in FIG. 25) and an open position 4055 (e.g., as shown in FIG. 33). In the open position 4055, the male coupling 2105 is coupled to the female coupling 2110 and the first male coupling internal channel 3025 and the second male coupling internal channel 4040 are in fluid connection via a male coupling cavity 4060 of the male coupling 2105 (e.g., as shown in FIG. 38). In the closed position 4050, fluid flow between the first male coupling internal channel 3025 and the second male coupling internal channel 4040 is prevented.

Referring now to FIG. 25, the male coupling member 4045 includes a bias spring 4065 and a reciprocating valve 4070. The bias spring 4065 includes a first end 4075 connected to a first stop surface 4080 of the male coupling 2105 and a second end 4085 connected to a valve stem 4090 of the reciprocating valve 4070. The reciprocating valve 4070 is normally biased closed in which a valve stem o-ring 4095 fitted to the valve stem 4090 is biased against a second stop surface 5000 of the male coupling 2105 by the bias spring 4065. In the example embodiment, a hollow fluid flow shaft 5005 of the reciprocating valve 4070 slidably positioned within the first male coupling internal channel 3025 partially extends from the first male coupling aperture 3015. In this position, fluid flow between the first male coupling internal channel 3025 and the second male coupling internal channel 4040 is prevented.

Referring now to FIGS. 25-31, the female coupling 2110 of the example assembly 2000 is shown. The female coupling 2110 is radially symmetric about a longitudinal axis U and generally includes a body 6000 formed as a receptacle section 6005 and a female coupling post section 6010. The female coupling 2110 further includes a first female coupling aperture 6015 and a second female coupling aperture 6020.

The receptacle section 6005 includes a receptacle outer surface 6025 and a receptacle inner surface 6030. The receptacle outer surface 6025 defines a contoured gripping surface to facilitate mating of the male coupling 2105 to the female coupling 2110. The first female coupling aperture 6015 is adjacent to an insertion cavity 6035 and is defined by a first receptacle periphery 6040 at a radial distance D6 measured with respect to the axis U. The first receptacle periphery 6040 is mechanically deformable to a radial distance greater than D6 to facilitate coupling and decoupling of the male coupling 2105 to the female coupling 2110.

The receptacle inner surface 6030 defines the insertion cavity 6035 including a beveled lead-in surface 6045 formed adjacent to the first receptacle periphery 6040, a rib engagement surface 6050, a sealing surface 6055, a rib retention groove 6060, a first retention surface 6065, and a second retention surface 6070. The rib engagement surface 6050 is generally a flat surface normally defined at a radial distance D7 measured with respect to the axis U. Similarly, the sealing surface 6055 is generally a flat surface normally defined at a radial distance D8 measured with respect to the axis U. The rib retention groove 6060 is flanked by the first retention surface 6065 and the second retention surface 6070 and is generally complementary to the geometry of the first arcuate rib 3070 and the second arcuate rib 3075 of the male coupling 2105.

The female coupling post section 6010 includes a post outer surface 6075 defining an elongated barbed post 6080 comprising a plurality of post barbs 6085. Each respective post barb 6085 tapers inwardly towards the axis U from a post barb end surface 6090 in a direction of the second female coupling aperture 6020. The barbed post 6080 facilitates secure connections to conduits (e.g., second conduit 160) running to various equipment or other applications. The second female coupling aperture 6020 is adjacent to the barbed post 6080 and is defined by a second receptacle periphery 6095. The second receptacle periphery 6095 is defined by a radial distance D9 corresponding to a channel surface 7000 of a female coupling internal channel 7005.

Figure 31:
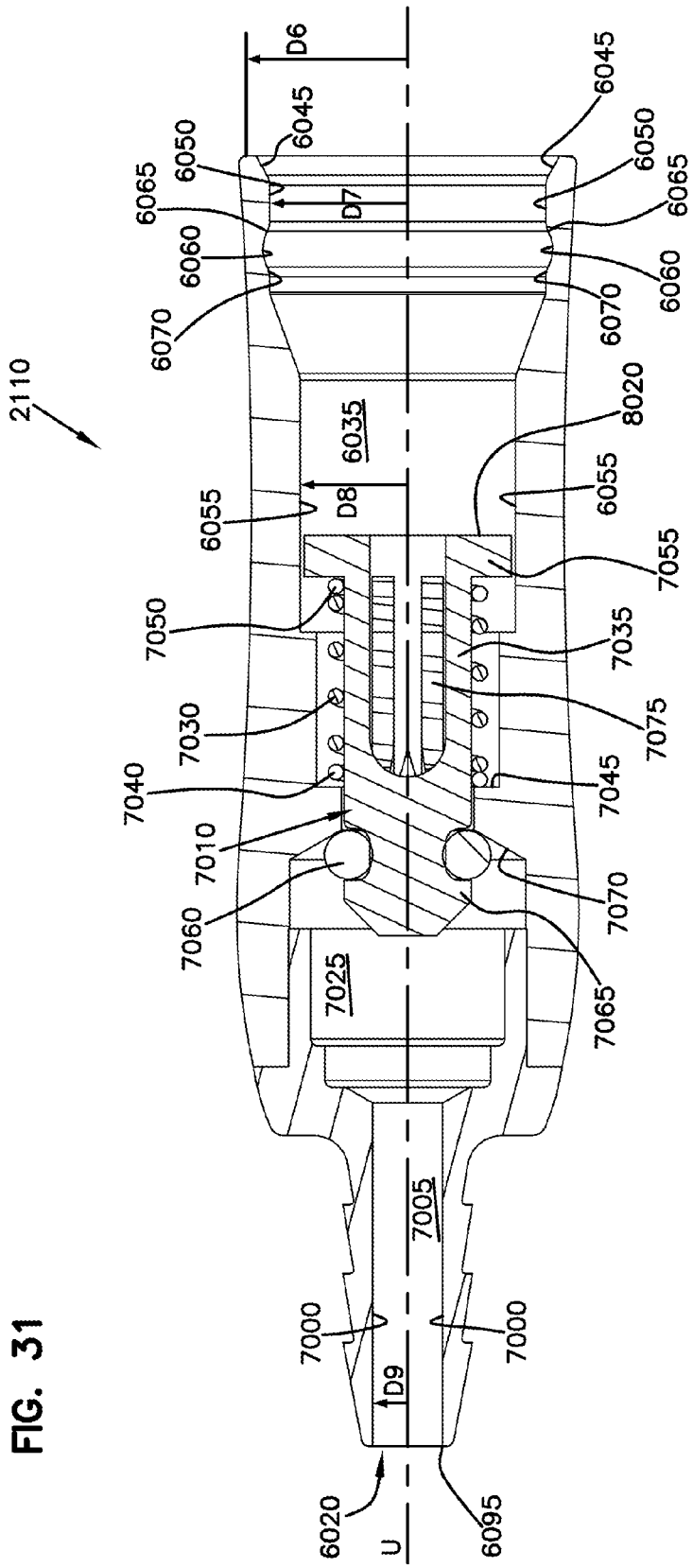
FIG. 31 is a cross-sectional view of the female coupling of FIG. 30.
Figure 32:
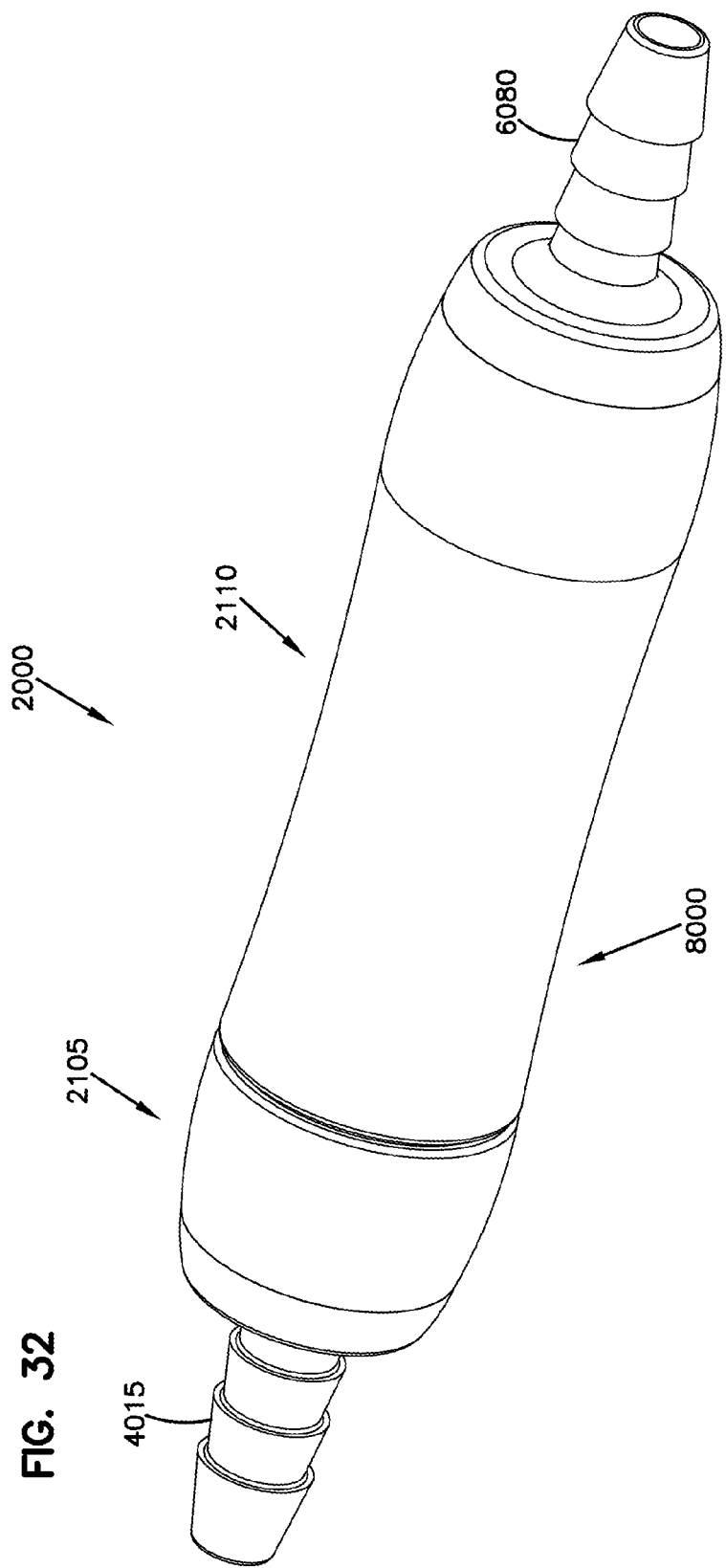
FIG. 32 is a perspective view of the example male coupling and female coupling of FIGS. 20-31 in a fully coupled state.

As mentioned above, the example assembly 2000 is a valved assembly. In example embodiments, the female coupling 2110 includes a female coupling valve 7010 that is actuated between a normally closed position 7015 (e.g., as shown in FIG. 31) and an open position 7020 (e.g., as shown in FIG. 33). In the open position 7020, the male coupling 2105 is coupled to the female coupling 2110 and the insertion cavity 6035 is in fluid connection with a female coupling cavity 7025 and the female coupling internal channel 7005, as described in further detail below in connection with FIGS. 32-40. In the normally closed position 7015, fluid flow between the insertion cavity 6035, female coupling cavity 7025, and female coupling internal channel 7005 is prevented.

Referring now to FIG. 31, the female coupling valve 7010 includes a bias spring 7030 and a reciprocating value 7035. The bias spring 7030 includes a first end 7040 connected to a first stop surface 7045 of the female coupling 2110 and a second end 7050 connected to a flange 7055 of the reciprocating value 7035. The reciprocating value 7035 is normally biased closed in which a valve stem o-ring 7060 fitted to a valve stem 7065 of the reciprocating value 7035 is biased against a second stop surface 7070 of the female coupling 2110 by the bias spring 7030. In the example embodiment, fluid flow between a hollow fluid flow shaft 7075 of the reciprocating value 7035 in connection with the insertion cavity 6035, female coupling cavity 7025, and female coupling internal channel 7005 is prevented.

Referring now to FIGS. 32-40, the male coupling 2105 and female coupling 2110 of the example assembly 2000 are shown in fully coupled state 8000 (FIGS. 32-34, 38) and a partially coupled state 8005 (FIGS. 35-37, 39, 40). The male coupling 2105 and the female coupling 2110 are aligned about a longitudinal axis V.

The male coupling 2105 and female coupling 2110 of the example assembly 2000 are coupled via a push-to-connect process to form a fluid tight pressure seal. Additionally, both the male coupling 2105 and female coupling 2110 are radially symmetric and are non-keyed such that the male coupling 2105 may be inserted into the female coupling 2110 in any radial orientation.

In example embodiments, male coupling 2105 and female coupling 2110 are coupled and decoupled from each other similar to the male coupling 205 and female coupling 210 described above with respect to FIGS. 9-12.

For example, as shown in FIGS. 35-37, 39, and 40, the male coupling 2105 is coupled to the female coupling 2110 by orientating the male coupling 2105 such that the insert post 3140 is pointing towards and inserted through the first female coupling aperture 6015 and into the insertion cavity 6035. This motion proceeds with minimal resistance until the rib engagement surface 3085 of the first arcuate rib 3070 and the second arcuate rib 3075 contact the lead-in surface 6045 of the female coupling 2110.

An initial application of force along the axis V is required for further insertion of the insert post 3140 into the insertion cavity 6035. Upon application of sufficient force, interaction of the rib engagement surface 3085 with the lead-in surface 6045 deforms the first receptacle periphery 6040 from a normally circular shape into an elliptical shape (e.g., see FIG. 36). The o-ring 3095 interacts with the sealing surface 6055 of the female coupling 2110 to form a fluid seal 8010.

The deformation surface 3080 of the first arcuate rib 3070 and the second arcuate rib 3075 contacts the rib engagement surface 3085 of the female coupling 2110 upon further application of force along the axis V. The deformation surface 3080 imparts an increasing load on the receptacle section 6005 in a direction normal and outward with respect to the axis V as the insert post 3040 is further inserted into the insertion cavity 6035. Similar to that described above with respect to the male coupling 205 and female coupling 210, an increased application of force is required to further position the insert post 3140 into the first female coupling aperture 6015 based on the magnitude of the radial distance D1. This proceeds until the retention surface 3090 of the first arcuate rib 3070 and the second arcuate rib 3075 engage with the first retention surface 6065 of the female coupling 2110. Upon engagement of the retention surface 3090 with the first retention surface 6065, the first arcuate rib 3070 and the second arcuate rib 3075 are forcefully drawn into the rib retention groove 6060 of the female coupling 2110 in a snap-action by virtue of rearrangement of load imparted on the receptacle section 6005 by the first arcuate rib 3070 and the second arcuate rib 3075 into force components both normal and coincident to the axis V.

In conjunction with the snap-action, a male leading surface 8015 (see e.g., FIG. 21) of the reciprocating valve 4070 of the male coupling member 4045 engages with a female leading surface 8020 (see e.g., FIG. 31) of the flange 7055 of the reciprocating value 7035 of the female coupling valve 7010. Upon this forceful engagement, the bias spring 4065 of the male coupling member 4045 and the bias spring 7030 of the female coupling valve 7010 are loaded with an equal and opposite force, which actuates the valve stem o-ring 4095 of the male coupling 2105 away from the second stop surface 5000 and the valve stem o-ring 7060 of the female coupling 2110 away from the second stop surface 7070. In this manner, the male coupling 205 and female coupling 210 are in the fully coupled state 8000 and a continuous fluid flow path F is formed between the second male coupling aperture 3020 and the second female coupling aperture 6020, as shown in FIGS. 32-34 and 38.

The male coupling 2105 is decoupled from the female coupling 2110 via application of a pinching force to the receptacle outer surface 6025 to deform the first receptacle periphery 6040 into an elliptical, release shape or by simply pulling the male coupling 2105 and female coupling 2110 in opposite directions with enough force. Subsequently, while maintaining the applied force to the receptacle outer surface 6025, the insert post 3140 of the male coupling 2105 is removed from the insertion cavity 6035 of female coupling 2110.

Figure 34:
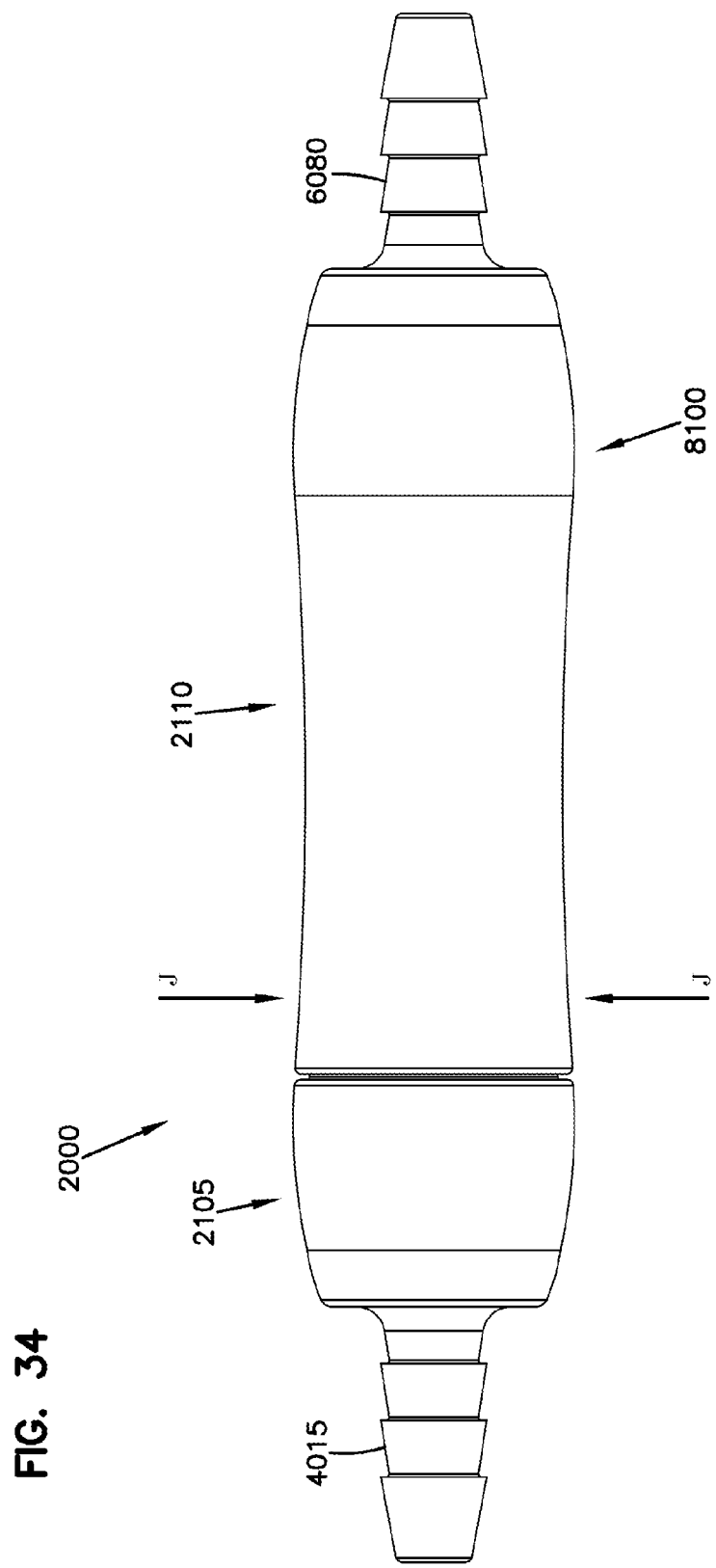
FIG. 34 is a side view of the male coupling and female coupling of FIG. 32.
Figure 35:
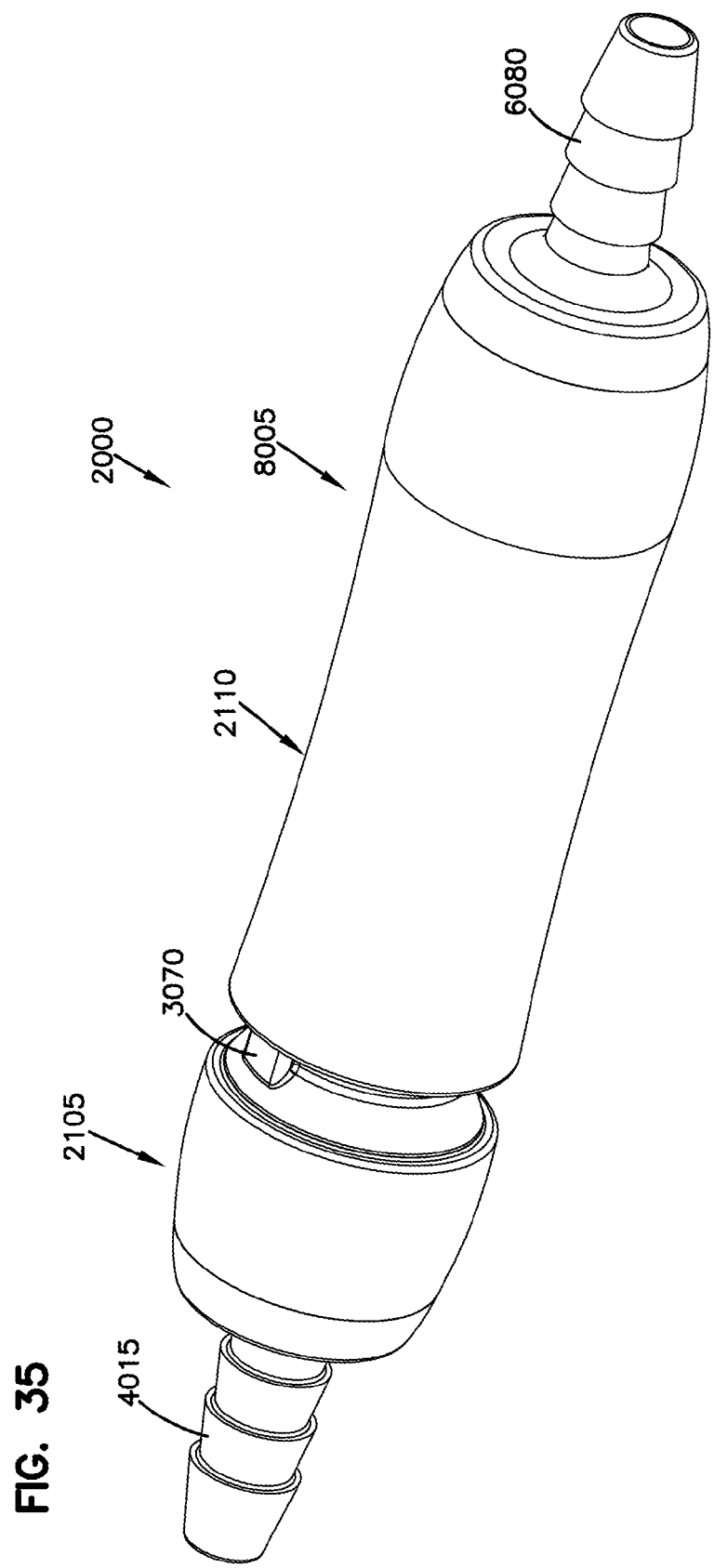
FIG. 35 is a perspective view of the male coupling and female coupling of FIG. 32 in a partially coupled state.
Figure 36:
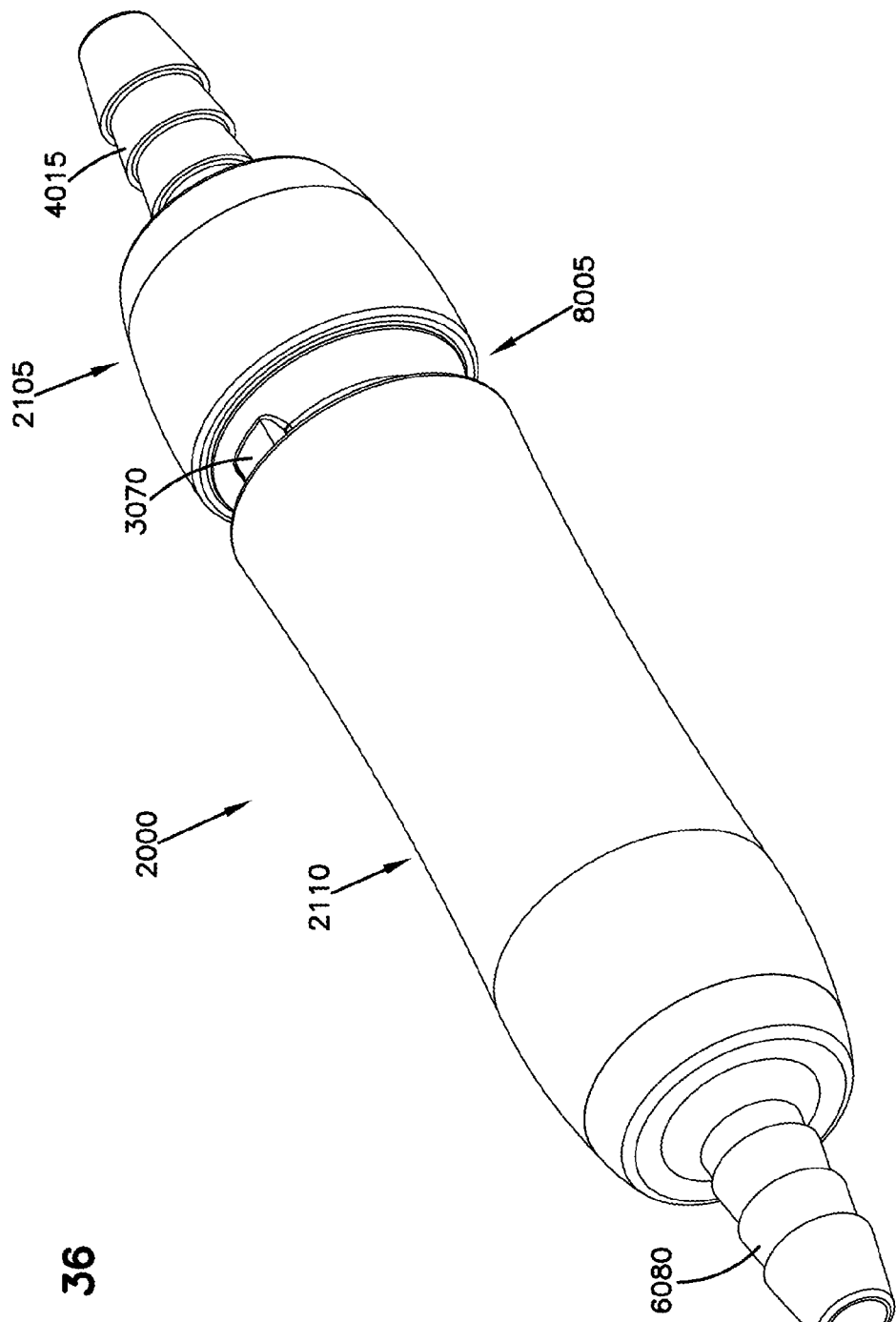
FIG. 36 is another perspective view of the male coupling and female coupling of FIG. 35.
Figure 37:
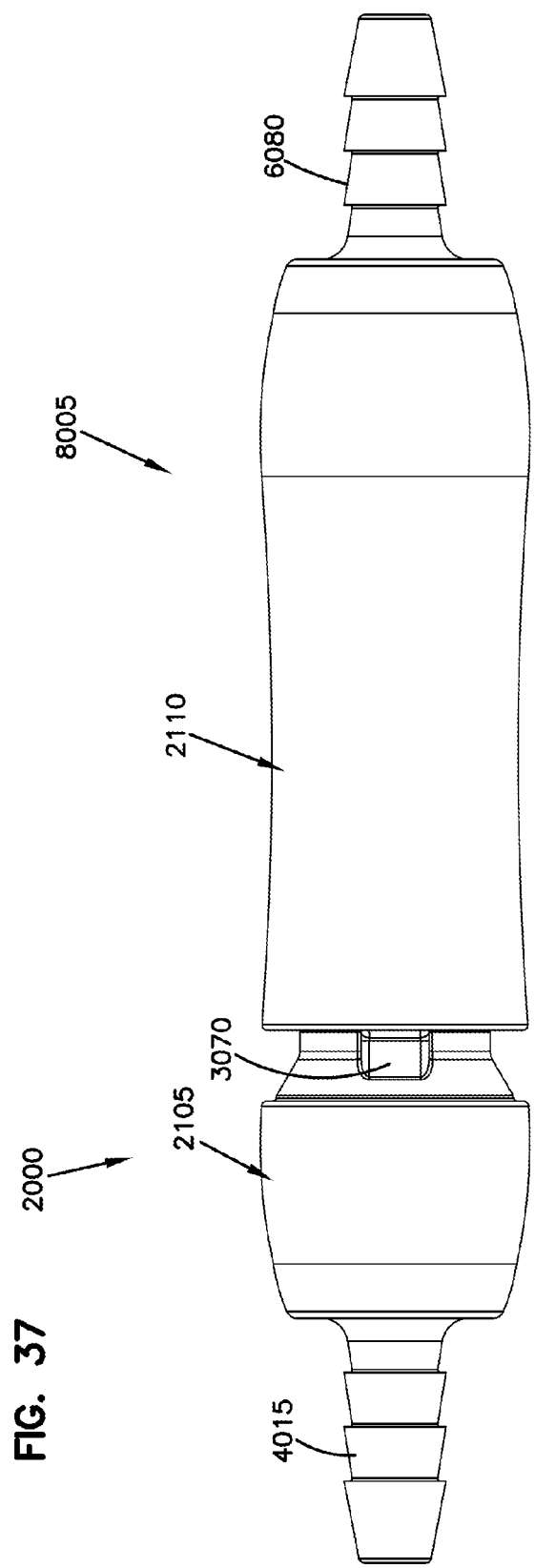
FIG. 37 is a side view of the male coupling and female coupling of FIG. 35.
Figure 40:
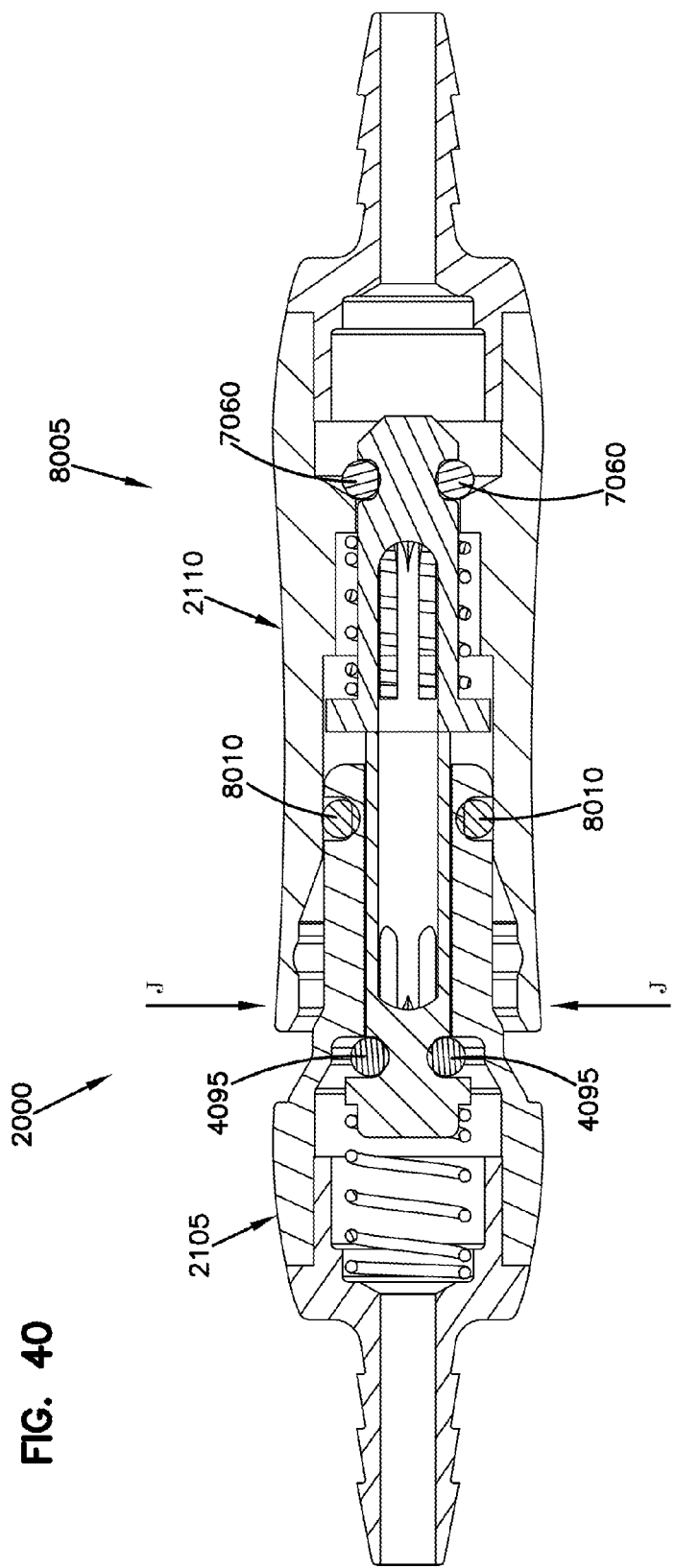
FIG. 40 is another cross-sectional view of the male coupling and female coupling of FIG. 39.

For example, referring specifically to FIGS. 34 and 40, a pinching force J may applied to the receptacle outer surface 6025 to deform the first the first receptacle periphery 6040 into the elliptical shape. While maintaining the applied pinching force J to receptacle outer surface 6025, the insert post 3040 of the male coupling 2105 is removed from the female coupling 2110 by pulling the male coupling 2105 away from the female coupling 2110 in a direction along the axis V. As the male coupling 2105 is pulled away from the female coupling 2110 the first receptacle periphery 6040 is deformed to an elliptical shape of similar eccentricity to the elliptical shape assumed by the first receptacle periphery 6040 when the male coupling 2105 is coupled to the female coupling 2110 as described above.

In example embodiments, the second end portion 3065 adjacent to the male coupling post section 3010 of the male coupling 2105 includes a beveled surface 3071. The beveled surface 3071 is sized to engage the first receptacle periphery 6040 of the female coupling 2110 in the fully connected state to maintain the round periphery of the first receptacle periphery 6040. This minimizes any tendency of the first receptacle periphery 6040 to form an oval shape due to any stress placed on the first receptacle periphery 6040 by the first and second ribs 3070, 3075.

In example embodiments, the male coupling and the female coupling of the first example breakaway coupling assembly 200 and the second example breakaway coupling assembly 2000 are made of a material such as a thermoplastic that provides for good structural integrity and surface finish. In one example, a thermoplastic such as acetal is used. Examples of other materials that can be used include, but are not limited to, polyvinyl chloride, nylon, polycarbonate, polyester, and Acrylonitrile-Butadiene-Styrene (ABS). Other materials can be used.

In example embodiments, the male coupling and the female coupling of the first example breakaway coupling assembly 200 and the second example breakaway coupling assembly 2000 are made using an injection molding process. In such an example, injection molding process, a resin is heated beyond the resin's melting point and injected into a steel or aluminum mold to form components of the assembly. Other potential methods of manufacture include, but are not limited to, machining the complete assembly or machining (or molding) components of the assembly and bonding them together. Other methods of manufacture can be used, such as die casting or metal injection molding.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A breakaway coupling assembly, comprising:
   a male coupling including an insert section and a post section, and defining a first male coupling aperture and a second male coupling aperture connected by a male coupling internal channel, the insert section including a sealing gasket and a plurality of ribs, each including a snap-action surface; and
   a female coupling including a receptacle section and a female coupling post section, and defining a mechanically deformable first female coupling aperture and a second female coupling aperture connected by a female coupling internal channel, the receptacle section defining an insertion cavity including a sealing surface, a rib retention groove, and a retention surface;
   wherein, upon insertion of the male coupling insert section into the insertion cavity, the plurality of ribs deforms the first female coupling aperture and the retention surface engages with the first retention surface to draw the plurality of ribs into the rib retention groove, and the sealing gasket engages the sealing surface to form a continuous fluid flow path for fluid to flow between the male coupling internal channel and the female coupling internal channel; and
   wherein the first female coupling aperture forms a complete circular periphery shape, and, upon insertion, the plurality of ribs forces the first female coupling aperture to form an elliptical periphery shape.

2. The breakaway coupling assembly of claim 1, wherein each of the male coupling and the female coupling includes a normally-closed valve assembly.

3. The breakaway coupling assembly of claim 1, wherein the male coupling further includes a beveled surface, the beveled surface configured to engage a first receptacle periphery defining the first female coupling aperture upon insertion of the male coupling insert section to the insertion cavity to maintain the first receptacle periphery as a circular periphery.

4. The breakaway coupling assembly of claim 1, wherein a relationship between the ribs and the rib retention groove are such that a desired amount of force is required to couple and decouple the male coupling and the female coupling.

5. The breakaway coupling assembly of claim 1, wherein the ribs include a first rib and a diametrically opposed second rib.

6. The breakaway coupling assembly of claim 5, wherein the first and second ribs are arcuate.

7. The breakaway coupling assembly of claim 6, wherein a relationship between the ribs and the rib retention groove are such that a desired amount of force is required to couple and decouple the male coupling and the female coupling.

8. A female breakaway coupling, comprising:
a receptacle section defining an insertion cavity including a sealing surface, a rib retention groove, and a retention surface;
a female coupling post section; and
a mechanically deformable first female coupling aperture and a second female coupling aperture connected by a female coupling internal channel;
wherein, upon insertion of a male breakaway coupling insert section into the insertion cavity, a plurality of ribs of the male breakaway coupling deforms the first female coupling aperture and the retention surface engages with a first retention surface of the male breakaway coupling to draw the plurality of ribs into the rib retention groove, and a sealing gasket of the male breakaway coupling engages the sealing surface to form a continuous fluid flow path for fluid to flow between the male breakaway coupling and the female coupling internal channel; and
wherein the first female coupling aperture forms a complete circular periphery shape, and, upon insertion, the plurality of ribs forces the first female coupling aperture to form an elliptical periphery shape.

9. The female breakaway coupling of claim 8, wherein a relationship the ribs and the rib retention groove are such that a desired amount of force is required to couple and decouple the male breakaway coupling and female breakaway coupling.

10. The female breakaway coupling of claim 8, wherein the female breakaway coupling includes a normally-closed valve assembly.

11. The female breakaway coupling of claim 10, wherein a relationship between the ribs and the rib retention groove are such that a desired amount of force is required to couple and decouple the male breakaway coupling and the female breakaway coupling.

12. A method of coupling a male coupling to a female coupling to form a breakaway coupling assembly, the method comprising:

providing a male coupling including an insert section and a post section, and defining a first male coupling aperture and a second male coupling aperture connected by a male coupling internal channel, the insert section including a sealing gasket and a plurality of ribs, each including a snap-action surface; and providing a female coupling including a receptacle section and a female coupling post section, and defining a mechanically deformable first female coupling aperture and a second female coupling aperture connected by a female coupling internal channel, the receptacle section defining an insertion cavity including a sealing surface, a rib retention groove, and a retention surface, wherein the first female coupling aperture forms a complete circular periphery shape;

inserting the male coupling insert section into the insertion cavity; and allowing the plurality of ribs to deform the first female coupling aperture so that the first female coupling aperture forms an elliptical periphery shape and the retention surface engages with the first retention surface to draw the plurality of ribs into the rib retention groove, and the sealing gasket engages the sealing surface to form a continuous fluid flow path for fluid to flow between the male coupling internal channel and the female coupling internal channel.

13. The method of claim 12, wherein each of the male coupling and the female coupling includes a normally-closed valve assembly.

14. The method of claim 12, wherein the male coupling further includes a beveled surface, the beveled surface configured to engage a first receptacle periphery defining the first female coupling aperture upon insertion of the male coupling insert section to the insertion cavity to maintain the first receptacle periphery as a circular periphery.

15. The method of claim 12, further comprising defining a relationship between the ribs and the rib retention groove so such that a desired amount of force is required to couple and decouple the male coupling and the female coupling.

16. The method of claim 12, wherein the ribs include a first rib and a diametrically opposed second rib.

17. The method of claim 16, wherein the first and second ribs are arcuate.

* * * * *